(12) United States Patent
Torikai et al.

(10) Patent No.: US 10,597,440 B2
(45) Date of Patent: Mar. 24, 2020

(54) ANTI-TRANSTHYRETIN HUMAN ANTIBODY

(71) Applicant: KM BIOLOGICS CO., LTD., Kumamoto (JP)

(72) Inventors: Masaharu Torikai, Kumamoto (JP); Akihiko Hosoi, Kumamoto (JP); Tomoyo Takeo, Kumamoto (JP); Masayo Ueno, Kumamoto (JP); Kenji Soejima, Kumamoto (JP); Toshihiro Nakashima, Kumamoto (JP); Yukio Ando, Kumamoto (JP); Hirofumi Jono, Kumamoto (JP); Yu Su, Shanghai (CN); Mineyuki Mizuguchi, Imizu (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 0 days.

(21) Appl. No.: 15/114,545

(22) PCT Filed: Jan. 23, 2015

(86) PCT No.: PCT/JP2015/051860
§ 371 (c)(1),
(2) Date: Jul. 27, 2016

(87) PCT Pub. No.: WO2015/115332
PCT Pub. Date: Aug. 6, 2015

(65) Prior Publication Data
US 2016/0340419 A1 Nov. 24, 2016

(30) Foreign Application Priority Data

Jan. 29, 2014 (JP) .................................. 2014-014912

(51) Int. Cl.
*C07K 16/18* (2006.01)
*A61K 39/395* (2006.01)
*G01N 33/68* (2006.01)
*C07K 16/00* (2006.01)
*A61K 39/00* (2006.01)

(52) U.S. Cl.
CPC .......... *C07K 16/18* (2013.01); *A61K 39/0007* (2013.01); *C07K 16/005* (2013.01); *G01N 33/6896* (2013.01); *A61K 2039/505* (2013.01); *C07K 2317/21* (2013.01); *C07K 2317/24* (2013.01); *C07K 2317/34* (2013.01); *C07K 2317/569* (2013.01); *C07K 2317/76* (2013.01); *G01N 2800/7047* (2013.01)

(58) Field of Classification Search
CPC ................ A61K 39/0007; C07K 16/18; C07K 2317/21; C07K 2317/565; C07K 14/00
See application file for complete search history.

(56) References Cited

U.S. PATENT DOCUMENTS

| 7,601,351 B1 | 10/2009 | Rosen et al. |
| 2004/0151721 A1 | 8/2004 | O'Keefe et al. |
| 2005/0164365 A1 | 7/2005 | Yonemura et al. |
| 2008/0153132 A1 | 6/2008 | Yonemura et al. |
| 2014/0056904 A1 | 2/2014 | Chakrabartty et al. |

FOREIGN PATENT DOCUMENTS

| JP | 2010-195710 | 9/2010 |
| WO | 03/004647 | 1/2003 |
| WO | 2009/055054 | 4/2009 |
| WO | 2009/086539 | 7/2009 |
| WO | 2010/030203 | 3/2010 |
| WO | 2013/126810 | 8/2013 |
| WO | 2014/124334 | 8/2014 |

OTHER PUBLICATIONS

Foote et al., J. Mol. Biol. 224 (1992): 487-499.*
Extended European Search Report dated Aug. 14, 2017 in corresponding European patent application No. 15743541.3.
G. Arsequell et al., Methods to Evaluate the Inhibition of TTR Fibrillogenesis Induced by Small Ligands, Current Medicinal Chemistry: The New International Journal for Timely In-Depth Reviews in Medicinal Chemistry, vol. 19, No. 15, Apr. 24, 2012, pp. 2343-2355.
Ignacio Dolado et al., Kinetic Assay for High-Throughput Screening of In Vitro Transthyretin Amyloid Fibrillogenesis Inhibitors, Journal of Combinatorial Chemistry, vol. 7, No. 2, Mar. 1, 2005, pp. 246-252.
Ricardo Sant'Anna et al., Inhibition of Human Transthyretin Aggregation by Non-Steroidal Anti-Inflammatory Compounds: A Structural and Thermodynamic Analysis, International Journal of Molecular Sciences, vol. 14, No. 3, Mar. 6, 2013, pp. 5284-5311.
Reixach N et al., Cell based screening inhibitors of transthyretin aggregation, Biochemical and Biophysical Research Communications, Elsevier, Amsterdam, NL, vol. 348, No. 3, Sep. 29, 2006, pp. 889-897.
International Search Report dated Apr. 14, 2015 in International Application No. PCT/JP2015/051860.
International Preliminary Report on Patentability dated Aug. 2, 2016 in International Application No. PCT/JP2015/051860.
George C. Glenner, M.D., Medical Progress, "Amyloid Deposits and Amyloidosis" The β-Fibrilloses, N. Engl J Med, vol. 302, No. 24, 1333-1343, 1980.

(Continued)

*Primary Examiner* — Robert C Hayes
(74) *Attorney, Agent, or Firm* — Wenderoth, Lind & Ponack, L.L.P.

(57) ABSTRACT

A human antibody which comprises a complementarity determining region of an H chain consisting of the amino acid sequence as shown in SEQ ID NOs: 1 to 3 and a complementarity determining region of an L chain consisting of the amino acid sequence as shown in SEQ ID NOs: 4 to 6. The human antibody of the present invention has the activity to specifically bind to transthyretin (TTR) with structural change and the activity to inhibit fibrillization of TTR and is a human antibody suitable for application to human body.

19 Claims, 11 Drawing Sheets

Specification includes a Sequence Listing.

(56) References Cited

OTHER PUBLICATIONS

Yukio Ando, MD et al., "Pathogenesis and Therapy for Transthyretin Related Amyloidosis", Rinsho Byori, 56, 114-120, 2008 with English abstract. Only.
Yoshiki Sekijima et al., "Molecular pathogenesis of TTR amyloidosis and its inhibition", Igaku-No-Ayumi, 229, 349-356, 2009 with partial English translation. Abstract Only.
Yuko Kato-Motozaki et al., "Molecular epidemiology of familial amyloid polyneuropathy", Igaku-No-Ayumi, 229, 357-362, 2009 with partial English translation. Abstract Only.
Xu Hou et al., "Transthyretin and familial amyloidotic polyneuropathy" Recent progress in understanding the molecular mechanism of neurodegeneration, FEBS J, 274, 1637-1650, 2007.
Shukuro Araki et al., Transthyretin-related familial amyloidotic polyneuropathy—Progress in Kumamoto, Japan (1967-2010)—, Proc. Jpn. Acad., Ser. B Phys Biol Sci, 86, 694-706, 2010.
Vasso Episkopou et al., "Disruption of the transthyretin gene results in mice with depressed levels of plasma retinol and thyroid hormone", Proc Natl Acad Sci USA, 90, 2375-2379, 1993.
Yukio Ando, "Liver transplantation and other therapies for familial amyloidotic polyneuropathy", Igaku-No-Ayumi, 229, 363-368, 2009 with partial English translation. Abstract only.
Gerard Said et al., "Tafamidis", Nat Rev Drug Discov, 11, 185-186, 2012.
Gundars Goldsteins et al., "Exposure of cryptic epitopes on transthyretin only in amyloid and in amyloidogenic mutants", Proc Natl Acad Sci USA, 96, 3108-3113, 1999.
Hisayasu Terazaki et al., "Immunization in familial amyloidotic polyneuropathy: counteracting deposition by immunization with a Y78F TTR mutant", Lab Invest, 86, 23-31, 2006.
Joakim Bergstrom et al., "Surface exposed epitopes and structural heterogeneity of in vivo formed transthyretin amyloid fibrils", Biochem Biophys Res Commun, 348, 532-539, 2006.
Kimiaki Matsubara et al., "Expression of a synthetic gene encoding human transthyretin in *Escherichia coli*", Protein Expr Purif, 30, 55-61, 2003.
Mitsuharu Ueda et al., "A transgenic rat with the human ATTR V30M: A Novel Tool for analyses of ATTR metabolisms", Biochem Biophys Res Commun, 352, 299-304, 2007.
Kimiaki Matsubara et al., "Dimeric Transthyretin Variant Assembles into Spherical Neurotoxins", Biochemistry, 44, 3280-3288, 2005.
S. Senju et al., "Generation of dendritic cells and macrophages from human induced pluripotent stem cells aiming at cell therapy", Gene Therapy, 18, 874-883, 2011.

Akihiko Hosoi., "Antibody Therapy for Familial Amyloidotic Polyneuropathy", Reimei, Oct. 1, 2012, vol. 21, pp. 47-51 with partial English translation. Abstract only.
M. Ueda et al., Iyaku (Medicine and Drug) Journal, 2012, vol. 48, No. 5, pp. 1307-1314 with partial English translation. Abstract only.
Y. Ando et al., Annual Review Shinkei (Nerve) 2011, pp. 310-317 with partial English translation. Abstract only.
H. Oba et al., Frontier of Development of Antibody Medicine, Jul. 20, 2007, pp. 157-169 with partial English translation. Abstract only.
Phay et al., "Transthyretin Aggregate-Specific Antibodies Recognize Cryptic Epitopes on Patient-Derived Amyloid Fibrils", Rejuvenation Research, 17(2):97-104 (2014).
Su et al., "Antibody therapy for familial amyloidotic polyneuropathy", Amyloid, 19(S1):45-46 (2012).
Gustavsson et al., "Mechanisms of Transthyretin Amyloidogenesis. Antigenic Mapping of Transthyretin Purified from Plasma and Amyloid Fibrils and within in Situ Tissue Localizations", American Journal of Pathology, 144(6):1301-1311 (1994).
Little, "Chapter 7—Therapeutic Antibodies from XenoMouse Transgenic Mice" from "Recombinant Antibodies for Immunotherapy", Cambridge University Press, Cambridge, UK, pp. 89-107 (2009).
Lonberg, "Human antibodies from transgenic animals", Nature Biotechnology, 23(9):1117-1125 (2005).
Hoogenboom, "Selecting and screening recombinant antibody libraries", Nature Biotechnology, 23(9):1105-1116 (2005).
Léger et al., "Humanization of Antibodies", Molecular Medicine and Medical Chemistry, pp. 1-23 (2011).
Almagro et al., "Humanization of Antibodies", Frontiers in Bioscience, Albertson, NY, US, 13:1619-1633 (2008).
Partial Supplementary European Search Report dated May 31, 2017 in corresponding European Application No. 15743541.3.
International Search Report dated Apr. 14, 2015 in International (PCT) Application No. PCT/JP2015/051856.
International Preliminary Report on Patentability dated Aug. 2, 2016 in International (PCT) Application No. PCT/JP2015/051856.
Extended European Search Report dated May 26, 2017 in European Application No. 15743230.3.
Chinese Office Action dated Sep. 25, 2018 in corresponding Chinese Application No. 201580017230.1, with English translation.
Office Action dated Jun. 26, 2018 issued in European patent application No. 15743230.3.
Office Action dated Aug. 20, 2018 issued in European patent application No. 15743541.3.

\* cited by examiner

SEQUENCE LISTING

<160> NUMBER OF SEQ ID NOS: 41

<210> SEQ ID NO 1
<211> LENGTH: 5
<212> TYPE: PRT
<213> ORGANISM: Homo sapiens

<400> SEQUENCE: 1

Ser Tyr Ala Met Ser
1               5

<210> SEQ ID NO 2
<211> LENGTH: 17
<212> TYPE: PRT
<213> ORGANISM: Homo sapiens

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 10
<212> TYPE: PRT
<213> ORGANISM: Homo sapiens

<400> SEQUENCE: 3

Gly Thr Arg Thr Asn Trp Tyr Phe Asp Leu
1               5                   10

<210> SEQ ID NO 4
<211> LENGTH: 13
<212> TYPE: PRT
<213> ORGANISM: Homo sapiens

<400> SEQUENCE: 4

Ser Gly Ser Arg Ser Asn Ile Gly Ser Asn Thr Val Asn
1               5                   10

<210> SEQ ID NO 5
<211> LENGTH: 7
<212> TYPE: PRT
<213> ORGANISM: Homo sapiens

<400> SEQUENCE: 5

Ser Asn Asn Gln Arg Pro Ser
1               5

<210> SEQ ID NO 6
<211> LENGTH: 11
<212> TYPE: PRT
<213> ORGANISM: Homo sapiens

<400> SEQUENCE: 6

Ala Ala Trp Asp Asp Ser Leu Tyr Gly Pro Val
1               5                   10

<210> SEQ ID NO 7
<211> LENGTH: 5
<212> TYPE: PRT
<213> ORGANISM: Homo sapiens

<400> SEQUENCE: 7

Ser Tyr Tyr Met His

-continued

<210> SEQ ID NO 8
<211> LENGTH: 17
<212> TYPE: PRT
<213> ORGANISM: Homo sapiens

<400> SEQUENCE: 8

Ile Ile Asn Pro Ser Gly Gly Ser Thr Ser Tyr Ala Gln Lys Phe Gln
1               5                   10                  15

Gly

<210> SEQ ID NO 9
<211> LENGTH: 13
<212> TYPE: PRT
<213> ORGANISM: Homo sapiens

<400> SEQUENCE: 9

Phe Gly Ser Ser Ser Arg Gly Asn Asp Ala Phe Asp Ile
1               5                   10

<210> SEQ ID NO 10
<211> LENGTH: 11
<212> TYPE: PRT
<213> ORGANISM: Homo sapiens

<400> SEQUENCE: 10

Ser Gly Asp Val Leu Ala Lys Lys Tyr Ala Arg
1               5                   10

<210> SEQ ID NO 11
<211> LENGTH: 7
<212> TYPE: PRT
<213> ORGANISM: Homo sapiens

<400> SEQUENCE: 11

Lys Asp Ser Glu Arg Pro Ser
1               5

<210> SEQ ID NO 12
<211> LENGTH: 10
<212> TYPE: PRT
<213> ORGANISM: Homo sapiens

<400> SEQUENCE: 12

Tyr Ser Ala Ala Asp Asn Lys Glu Ala Val
1               5                   10

<210> SEQ ID NO 13
<211> LENGTH: 119
<212> TYPE: PRT
<213> ORGANISM: Homo sapiens

<400> SEQUENCE: 13

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Thr Arg Thr Asn Trp Tyr Phe Asp Leu Trp Gly Arg Gly
            100                 105                 110

Thr Leu Val Thr Val Ser Ser
            115

<210> SEQ ID NO 14
<211> LENGTH: 110
<212> TYPE: PRT
<213> ORGANISM: Homo sapiens

<400> SEQUENCE: 14

Ser Tyr Glu Leu Thr Gln Pro Pro Ser Ala Ser Gly Thr Pro Gly Gln
 1               5                  10                  15

Arg Val Thr Ile Ser Cys Ser Gly Ser Arg Ser Asn Ile Gly Ser Asn
                20                  25                  30

Thr Val Asn Trp Tyr Gln Gln Val Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Glu Tyr Tyr Cys Ala Ala Trp Asp Asp Ser Leu
                 85                  90                  95

Tyr Gly Pro Val Phe Gly Gly Gly Thr Gln Leu Thr Val Leu
            100                 105                 110

<210> SEQ ID NO 15
<211> LENGTH: 122
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ser Phe Gly Ser Ser Ser Arg Gly Asn Asp Ala Phe Asp Ile Trp
            100                 105                 110

Gly Gln Gly Thr Met Val Thr Val Ser Ser
            115                 120

<210> SEQ ID NO 16
<211> LENGTH: 107
<212> TYPE: PRT
<213> ORGANISM: Homo sapiens
```

<400> SEQUENCE: 16

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Lys Glu Ala
                85                  90                  95

Val Phe Gly Gly Gly Thr Gln Leu Thr Val Leu
            100                 105

<210> SEQ ID NO 17
<211> LENGTH: 27
<212> TYPE: DNA
<213> ORGANISM: Artificial
<220> FEATURE:
<223> OTHER INFORMATION: primer

<400> SEQUENCE: 17
cgcggatccg gccctacggg caccggt                                       27

<210> SEQ ID NO 18
<211> LENGTH: 36
<212> TYPE: DNA
<213> ORGANISM: Artificial
<220> FEATURE:
<223> OTHER INFORMATION: primer

<400> SEQUENCE: 18
cccaagcttt tatcattcct tgggattggt gacgac                             36

<210> SEQ ID NO 19
<211> LENGTH: 48
<212> TYPE: DNA
<213> ORGANISM: Artificial
<220> FEATURE:
<223> OTHER INFORMATION: primer

<400> SEQUENCE: 19
tgttgctatt ctcgagggtg tccagtgtga ggtgcagctg gtggagtc                48

<210> SEQ ID NO 20
<211> LENGTH: 36
<212> TYPE: DNA
<213> ORGANISM: Artificial
<220> FEATURE:
<223> OTHER INFORMATION: primer

<400> SEQUENCE: 20
ggggtgtcgt tttcgctgag gagacggtga ccaggg                             36

<210> SEQ ID NO 21
<211> LENGTH: 40
<212> TYPE: DNA
<213> ORGANISM: Artificial
<220> FEATURE:
<223> OTHER INFORMATION: primer

<400> SEQUENCE: 21
gggtcccagg ctcgagtggg tcctatgagc tgacacagcc      40

<210> SEQ ID NO 22
<211> LENGTH: 44
<212> TYPE: DNA
<213> ORGANISM: Artificial
<220> FEATURE:
<223> OTHER INFORMATION: primer

<400> SEQUENCE: 22
aagcgtattt ggatccactc acctaggacg gtcagctggg tgcc      44

<210> SEQ ID NO 23
<211> LENGTH: 48
<212> TYPE: DNA
<213> ORGANISM: Artificial
<220> FEATURE:
<223> OTHER INFORMATION: primer

<400> SEQUENCE: 23
tgttgctatt ctcgagggtg tccagtgtca aatgcagctg gtgcagtc      48

<210> SEQ ID NO 24
<211> LENGTH: 39
<212> TYPE: DNA
<213> ORGANISM: Artificial
<220> FEATURE:
<223> OTHER INFORMATION: primer

<400> SEQUENCE: 24
ggggtgtcgt tttcgctgaa gagacggtga ccattgtcc      39

<210> SEQ ID NO 25
<211> LENGTH: 48
<212> TYPE: DNA
<213> ORGANISM: Artificial
<220> FEATURE:
<223> OTHER INFORMATION: primer

<400> SEQUENCE: 25
tgttgctatt ctcgagggtg tccagtgtca ggtccagctg gtacagtc      48

<210> SEQ ID NO 26
<211> LENGTH: 15
<212> TYPE: DNA
<213> ORGANISM: Homo sapiens

<400> SEQUENCE: 26
agctatgcca tgagc      15

<210> SEQ ID NO 27
<211> LENGTH: 51
<212> TYPE: DNA
<213> ORGANISM: Homo sapiens

<400> SEQUENCE: 27
gctattagtg gtagtggtgg tagcacatac tacgcagact ccgtgaaggg c      51

<210> SEQ ID NO 28
<211> LENGTH: 30
<212> TYPE: DNA
<213> ORGANISM: Homo sapiens

<400> SEQUENCE: 28

```
gggacccgga cgaactggta cttcgatctc                              30

<210> SEQ ID NO 29
<211> LENGTH: 39
<212> TYPE: DNA
<213> ORGANISM: Homo sapiens

<400> SEQUENCE: 29
tctggaagta gatccaacat cgggagtaat actgttaac                    39

<210> SEQ ID NO 30
<211> LENGTH: 21
<212> TYPE: DNA
<213> ORGANISM: Homo sapiens

<400> SEQUENCE: 30
agtaataatc agcggccctc a                                       21

<210> SEQ ID NO 31
<211> LENGTH: 33
<212> TYPE: DNA
<213> ORGANISM: Homo sapiens

<400> SEQUENCE: 31
gcagcatggg atgacagtct gtatggtcct gtg                          33

<210> SEQ ID NO 32
<211> LENGTH: 15
<212> TYPE: DNA
<213> ORGANISM: Homo sapiens

<400> SEQUENCE: 32
agctactata tgcac                                              15

<210> SEQ ID NO 33
<211> LENGTH: 51
<212> TYPE: DNA
<213> ORGANISM: Homo sapiens

<400> SEQUENCE: 33
ataatcaacc ctagtggtgg tagcacaagc tacgcacaga agttccaggg c       51

<210> SEQ ID NO 34
<211> LENGTH: 39
<212> TYPE: DNA
<213> ORGANISM: Homo sapiens

<400> SEQUENCE: 34
ttcgggtctt ctagcagggg gaatgatgct tttgatatc                    39

<210> SEQ ID NO 35
<211> LENGTH: 33
<212> TYPE: DNA
<213> ORGANISM: Homo sapiens

<400> SEQUENCE: 35
tcaggagatg tactggcaaa aaaatatgct cgg                          33

<210> SEQ ID NO 36
<211> LENGTH: 21
<212> TYPE: DNA
<213> ORGANISM: Homo sapiens
```

```
<400> SEQUENCE: 36
aaagacagtg agcggccctc a                                          21

<210> SEQ ID NO 37
<211> LENGTH: 30
<212> TYPE: DNA
<213> ORGANISM: Homo sapiens

<400> SEQUENCE: 37
tactctgcgg ctgacaacaa ggaggctgtg                                 30

<210> SEQ ID NO 38
<211> LENGTH: 357
<212> TYPE: DNA
<213> ORGANISM: Homo sapiens

<400> SEQUENCE: 38
gaggtgcagc tggtggagtc cggggggaggc gtggtccagc ctgggggtc cctgagactc    60 tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgtat attactgtgc gaaagggacc   300
cggacgaact ggtacttcga tctctggggc cgtggcaccc tggtcaccgt ctcctca     357

<210> SEQ ID NO 39
<211> LENGTH: 330
<212> TYPE: DNA
<213> ORGANISM: Homo sapiens

<400> SEQUENCE: 39
tcctatgagc tgacacagcc accctcagcg tctgggaccc ccgggcagag ggtcaccatc    60
tcttgttctg gaagtagatc caacatcggg agtaatactg ttaactgtga ccaacaggtc   120
ccaggaacgg cccccaaact cctcatttat agtaataatc agcggccctc agggggtccct  180 gaccgattct ctggctccaa gtctggcacc tcagcctccc tggccatcag tggactccag   240
tctgaggatg aggctgaata ttattgtgca gcatgggatg acagtctgta tggtcctgtg   300
ttcggaggag gcacccagct gaccgtccta                                    330

<210> SEQ ID NO 40
<211> LENGTH: 366
<212> TYPE: DNA
<213> ORGANISM: Homo sapiens

<400> SEQUENCE: 40
caggtccagc tggtacagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccctca gtggtggtag cacaagctac   180
gcacagaagt tccagggcag agtcaccatg accagggaca cgtccacgag cacagtctac   240
atggagctga gcagcctgag atctgaggac acggccgtgt attactgtgc gagtttcggg   300
tcttctagca gggggaatga tgcttttgat atctgggggcc aagggacaat ggtcaccgtc   360
tcttca                                                              366

<210> SEQ ID NO 41
<211> LENGTH: 321
```

```
<212> TYPE: DNA
<213> ORGANISM: Homo sapiens

<400> SEQUENCE: 41
tcctatgagc tgacacagcc atcctcagtg tcagtgtctc cgggacagac agccaggatc      60
acctgctcag gagatgtact ggcaaaaaaa tatgctcggt ggttccagca gaagccaggc     120
caggcccctg tgctggtgat ttataaagac agtgagcggc cctcagggat ccctgagcga     180
ttctccggct ccagctcagg gaccacagtc accttgacca tcagcggggc ccaggttgag     240
gatgaggctg actattactg ttactctgcg gctgacaaca aggaggctgt gttcggagga     300
ggcacccagc tgaccgtcct a                                                321
```

ANTI-TRANSTHYRETIN HUMAN ANTIBODY

TECHNICAL FIELD

The present invention provides an antibody that effectively suppresses formation of amyloid fibril and its deposition to tissues by transthyretin (TTR) as well as a therapeutic method using said antibody. This antibody therapy is based on new therapeutic strategy that normal TTR is not affected but only amyloidogenesis of abnormal TTR is suppressed and is expected to be a novel therapeutic method excellent in safety.

BACKGROUND ART

Amyloidosis is a series of diseases where proteins forming a fiber structure are deposited in the whole-body organs to induce functional disturbance and includes various diseases such as Alzheimer dementia and prion disease (Non-patent reference 1).

Familial Amyloidotic Polyneuropathy (FAP) is autosomal dominant, hereditary, systemic amyloidosis caused by point mutation or deletion of genes of TTR, apolipoprotein A1, gelsolin and the like (Non-patent reference 2). Among these, FAP caused by genetic mutation of TTR is most common. It is known that mutant TTRs form amyloid fibril which is normally deposited in almost all the tissues of the whole body such as the peripheral nerve, the heart, the kidney, the digestive tract, the eye, the brain and the meninges after middle age. It is an intractable disease which shows very bad convalescence of patients and is mortal within around 10 years after onset of disease.

Up till the present, more than 100 point mutations and deletions of TTR gene have been reported. In particular, Val30Met mutation (hereinafter referred to as "V30M"), in which the 30th valine in TTR is mutated to methionine, is most common. There are many patients in Portugal, Sweden and Japan. Since more than 6,000 cases of FAP patients have been confirmed in Portugal, there are not a small number of regions where FAP has not yet been investigated and it is expected that worldwide discovery of FAP patients will continue, it is supposed that there are well over 10,000 patients all over the world. It became known from the recent research that the clinical picture (age of onset, deposit organ specificity, etc.) of FAP is greatly affected by the kind of mutation of TTR gene (Non-patent reference 3). For instance, with regard to age of onset of FAP, L55P mutation shows fulminant clinical picture that the disease develops in one's teens whereas with V122I mutation the disease develops at sixty and thereafter. On the other hand, it is known that V30M mutation shows both types of disease where the disease develops at a younger age and at an older age. With regard to deposit organ specificity, D18G mutation causes deposition at the brain and the meninges to cause central nerves disturbance whereas V30M mutation causes deposition in the whole-body tissues to cause peripheral nerves disturbance and myocardial disturbance (Non-patent references 3 and 4).

TTR is a protein that consists of 127 amino acid residues with a molecular weight of 14 kDa and has a structure that eight β-strands present inside form two antiparallel β-sheets (Non-patent reference 5). TTR is produced predominantly in the liver but also in the ventricular choroid plexus, the retinal pigment epithelium cells of retina, the spleen, and the like. TTR usually forms a stable structure by forming a tetramer with a molecular weight of 55 kDa in blood and functions as a carrier of a vitamin A/retinol-binding protein complex and thyroid hormone T4 mainly in blood and cerebrospinal fluid. Its blood level is as high as 200-400 μg/mL but its half-life is as short as 2 days (Non-patent references 2-6). It is known that in the center of a TTR tetramer are present two homologous T4-binding sites to which T4 binds to stabilize the tetramer structure (Non-patent reference 3). There are various reports about another function of TTR such as the insulin secretion promoting activity, the cerebral nerve protecting activity, and the activity relating to lipid metabolism (Non-patent reference 2). On the other, although a blood level of retinol and thyroid hormone decreases in TTR gene knockout mice, no significant change in phenotypes such as a survival rate and fertility property could be seen (Non-patent reference 7) and thus it remains unknown whether TTR is directly essential for maintenance of actual biological activity.

For amyloidogenesis by TTR, dissociation from a tetramer to a monomer and structural change of a monomer are very important steps (Non-patent reference 3). Among these, it has been revealed that dissociation from a tetramer to a monomer is a rate-determining step of the reaction. On the other hand, in the course where TTR forms amyloid that deposits in the tissues and damages the whole-body organs, a molecular form that exerts toxicity to the tissues has not yet been fully elucidated. It is reported that a monomer and a low molecular weight oligomer such as a dimer exhibit cytotoxicity whereas TTR amyloid of 100 kDa or more dose not (Non-patent reference 5) and so it is to be hoped that future research will clarify relationship between toxicity and a molecular form.

Therapeutic strategy for FAP originating from genetic anomaly of TTR is chiefly classified into the following four groups.

(1) To suppress a produced level of variant TTRs
(2) To stabilize a TTR tetrameric structure containing variant TTRs
(3) To prevent amyloid formation of TTR dissociated from a tetramer
(4) To remove TTR amyloid deposited in tissues Since almost all TTRs in blood are produced in the liver (Non-patent reference 2), the most common therapy at present is liver transplantation as classified in (1) above. Although delay in progression of the disease is observed by liver transplantation, it is inevitable to use an immunosuppressant through life with a great burden to donors and patients. Besides, deposition still continues in several organs including the eyes and the heart and thus exacerbation of symptoms in these organs can be seen in not a few cases (Non-patent reference 8). As such, it is problematic and hence development of an effective therapeutic method is earnestly desired.

For other therapeutic methods than liver transplantation, therapeutic methods using siRNA or an antisense oligonucleotide is at a stage of clinical development in case of the strategy (1). However, with all these methods, production of not only variant TTRs but also wild-type TTR is suppressed and thus their safety assessment when used for a long period of time should carefully be done. As for the strategy (2), a medicament has been developed that binds to the T4-binding sites of a TTR tetramer to thereby stabilize the tetrameric structure. The new medicine Vyndaqel® developed in accordance with the strategy has been approved in EU in 2011 and in Japan in 2013. As the result of clinical test for as long as 30 months, Vyndaqel® exhibited the effect to delay peripheral neuropathy in FAP patients but failed to suppress completely the progress of symptoms (Non-patent reference 9). Also for the strategies (3) and (4), although plural kinds of medicaments are at a stage of clinical development, the status quo is that none of the therapies can be a radical treatment.

PATENT REFERENCES

Patent reference 1: WO 2010030203
Patent reference 2: JP 2010-195710

NON-PATENT REFERENCES

Non-patent reference 1: Glenner, G. G.: Amyloid deposits and amyloidosis: the beta-fibrilloses (second of two parts): N Engl J Med, 302:1333-1343, 1980

Non-patent reference 2: Ando, Y. & Jono, H.: Pathogenesis and therapy for transthyretin related amyloidosis: Rinsho Byori, 56:114-120, 2008

Non-patent reference 3: Yoshiki Sekijima: Molecular mechanism of TTR amyloid deposition and its control: Igaku-No-Ayumi, 229:349-356, 2009

Non-patent reference 4: Yuko Motozaki, Shoji Yamada: Molecular epidemiology of familial amyloidotic polyneuropathy (FAP): Igaku-No-Ayumi, 229:357-362, 2009

Non-patent reference 5: Hou, X., Aguilar, M. I. & Small, D. H.: Transthyretin and familial amyloidotic polyneuropathy. Recent progress in understanding the molecular mechanism of neurodegeneration: FEBS J, 274:1637-1650, 2007

Non-patent reference 6: Araki, S. & Ando, Y.: Transthyretin-related familial amyloidotic polyneuropathy—Progress in Kumamoto, Japan (1967-2012): Proc Jpn Acad Ser B Phys Biol Sci, 86:694-706, 2010

Non-patent reference 7: Episkopou, V., Maeda, S., Nishiguchi, S., Shimada, K., Gaitanaris, G. A., Gottesman, M. E. & Robertson, E. J.: Disruption of the transthyretin gene results in mice with depressed levels of plasma retinol and thyroid hormone: Proc Natl Acad Sci USA, 90:2375-2379, 1993

Non-patent reference 8: Yukio Ando: Liver transplantation and other treatments for familial amyloidotic polyneuropathy (FAP): Igaku-No-Ayumi, 229:363-368, 2009

Non-patent reference 9: Said, G., Grippon, S. & Kirkpatrick, P.: Tafamidis: Nat Rev Drug Discov, 11:185-186, 2012

Non-patent reference 10: Goldsteins, G., Persson, H., Andersson, K., Olofsson, A., Dacklin, I., Edvinsson, A., Saraiva, M. J. & Lundgren, E.: Exposure of cryptic epitopes on transthyretin only in amyloid and in amyloidogenic mutants: Proc Natl Acad Sci USA, 96:3108-3113, 1999

Non-patent reference 11: Terazaki, H., Ando, Y., Fernandes, R., Yamamura, K., Maeda, S. & Saraiva, M. J.: Immunization in familial amyloidotic polyneuropathy: counteracting deposition by immunization with a Y78F TTR mutant: Lab Invest, 86:23-31, 2006

Non-patent reference 12: Bergstroem, J., Engstroem, U., Yamashita, T., Ando, Y. & Westermark, P.: Surface exposed epitopes and structural heterogeneity of in vivo formed transthyretin amyloid fibrils: Biochem Biophys Res Commun, 348:532-539, 2006

Non-patent reference 13: Matsubara, K., Mizuguchi, M. & Kawano, K.: Expression of a synthetic gene encoding human transthyretin in *Escherichia coli*: Protein Expr Purif, 30:55-61, 2003.

Non-patent reference 14: Ueda, M., Ando, Y., Hakamata, Y., Nakamura, M., Yamashita, T., Obayashi, K., Himeno, S., Inoue, S., Sato, Y., Kaneko, T., Takamune, N., Misumi, S., Shoji, S., Uchino, M. & Kobayashi, E.: A transgenic rat with the human ATTR V30M: a novel tool for analyses of ATTR metabolisms: Biochem Biophys Res Commun, 352:299-304, 2007.

Non-patent reference 15: Matsubara, K., Mizuguchi, M., Igarashi, K., Shinohara, Y., Takeuchi, M., Matsuura, A., Saitoh, T., Mori, Y., Shinoda, H. & Kawano, K.: Dimeric transthyretin variant assembles into spherical neurotoxins: Biochemistry, 44:3280-3288, 2005.

Non-patent reference 16: Senju, S., Haruta, M., Matsumura, K., Matsunaga, Y., Fukushima, S., Ikeda, T., Takamatsu, K., Irie, A. & Nishimura, Y.: Generation of dendritic cells and macrophages from human induced pluripotent stem cells aiming at cell therapy: Gene Ther, 18:874-883, 2011.

DISCLOSURE OF THE INVENTION

Technical Problem to be Solved by the Invention

In recent years, FAP treatment by immunotherapy draws attention. It became apparent that, in the course of formation of TTR amyloid, a new epitope (Cryptic Epitope) is exposed on the molecular surface in association with structural change of TTR (Non-patent reference 10).

Under such circumstances, Terazaki et al. immunized human TTR V30M transgenic mice (hTTR Tg mice), a model animal for FAP, with TTR Y78F variant, a variant known as exposing Cryptic Epitope, and assessed its effect on TTR amyloid deposition in mouse tissues (Non-patent reference 11). As a result, the significant increase in an antibody titer of an anti-TTR antibody was confirmed in the group of mice immunized with TTR Y78F variant and, along with this, the decrease in a deposited amount of TTR in the esophagus, the stomach and the intestines could be seen. Likewise, in the similar test with hTTR Tg mice of 18-month old that have already shown TTR deposition, the significant decrease in a deposited amount of TTR could be seen in the Y78F immunization group. These results suggested the possibility that immunization of mice with a TTR variant which exposes Cryptic Epitope induced production of an antibody against TTR in the body of mice and as a consequence TTR amyloid deposition was suppressed.

On the other hand, Bergstroem et al. immunized rabbits with a TTR 115-124 peptide, which is one of Cryptic Epitope, to prepare an anti-TTR115-124 polyclonal antibody (Non-patent reference 12). This polyclonal antibody was administered to hTTR V30M transgenic rats to assess the effect on TTR deposition in rat tissues. As a result, it was found that a deposited amount of TTR in the intestinal tracts of rat significantly decreased in the group with administration of the polyclonal antibody (Non-patent reference 13).

From these results, there may be the possibility that an antibody specifically recognizing Cryptic Epitope of TTR specifically binds to TTR amyloid (or TTR with structural change that constitutes TTR amyloid) to thereby promote inhibition of formation or removal of TTR amyloid. Namely, the possibility is suggested that an antibody specifically recognizing Cryptic Epitope of TTR can be a novel therapeutic agent of FAP.

Research of an anti-TTR antibody based on this concept was reported by BIOCODEX. BIOCODEX prepared mouse monoclonal antibody AD7F6, which is specific to amyloidogenetic TTR, using TTR knockout mice and showed that the monoclonal antibody suppressed tissue deposition of TTR using Tg mice (ATTR V30M), a disease model of FAP (Patent reference 1). The patent of BIOCODEX claims an amino acid sequence of the mouse antibody and thus it is difficult to administer the antibody to humans. It is not clearly described as to the reactivity of this antibody with V30M variant having a tetrameric structure. In FAP patients having V30M mutation, V30M variant in blood having a tetrameric structure is thought to be dissociated to monomers, a portion of which causes structural change to form amyloid. It is thus the requisites for realizing a more effective and safer antibody therapy to be an antibody that does not react with V30M variant having a tetrameric structure but reacts only with such V30M variant that formed amyloid (or that is in the midst of amyloidogenesis). With regard to the reactivity of this antibody, since only serum of V30M carriers is used as a clinical sample, its reactivity with tissue-depositing amyloid in the body of patients is unknown.

Research of an anti-TTR antibody based on the same concept was reported by the group of Porto University in Portugal (Non-patent reference 10). It reported that mouse monoclonal antibodies mAb 39-44 and mAb 56-61 were prepared which were specific to TTR with structural change and that these antibodies reacted with amyloid of V30M variant derived from the living body. It is stated clearly, however, that these antibodies did not show an inhibitory activity to amyloidogenesis and only the possibility of their use for FAP diagnosis is referred to.

As described above, although polyclonal antibodies or monoclonal antibodies obtained by immunization of mice (or rats) with Cryptic Epitope of TTR were reported to suppress TTR deposition, an antibody having the activity to specifically bind to TTR with structural change or the activity to inhibit TTR-fibrillization and a humanized antibody or a human antibody suitable for administration to humans were not reported.

Means for Solving the Problems

The present inventors recognized that in TTR amyloidosis a portion of tetrameric TTRs is dissociated into monomeric TTRs which undergo structural change to form amyloid but on the other hand there remain tetrameric TTRs which function normally. Thus, the present inventors have investigated an antibody that specifically binds to TTRs with structural change and has the activity to inhibit TTR-fibrillization. Aiming at achieving antibody therapy to TTR amyloidosis as a final goal, the present inventors have diligently investigated a human antibody having the above activity to complete the present invention.

Namely, the present invention relates to the followings:
(1) A human antibody having the activity to inhibit fibrillization of transthyretin (hereinafter referred to as "TTR");
(2) The human antibody of (1) which specifically recognizes TTRs with structural change;
(3) The human antibody of (1) or (2) which specifically binds to TTR amyloid;
(4) The human antibody of any one of (1) to (3) which binds to TTR amyloid derived from two or more kinds of variant TTRs;
(5) The human antibody of (4) wherein the variant TTR is TTR having a mutation selected from the group consisting of D18G, V30M, E54K, L55P, Y114C, Y116S and V122I;
(6) The human antibody of any one of (1) to (5) which promotes removal of TTR amyloid;
(7) The human antibody of any one of (1) to (6) which promotes the phagocytic ability of macrophages to TTR amyloid;
(8) The human antibody of any one of (1) to (7) wherein an epitope is a sequence comprising position 79 to position 89 of TTR;
(9) The human antibody of (8) wherein an epitope is position 79 to position 89 of TTR;
(10) The human antibody of any one of (1) to (9) which has a therapeutic effect and/or a preventive effect to TTR amyloidosis;
(11) The human antibody of (10) wherein the TTR amyloidosis is Familial Amyloidotic Polyneuropathy (hereinafter referred to as "FAP");
(12) The human antibody of (10) wherein the TTR amyloidosis is Senile Systemic Amyloidosis (hereinafter referred to as "SSA");
(13) The human antibody of any one of (1) to (12) which is an antibody obtained by phage display;
(14) The human antibody of any one of (1) to (13) which comprises a complementarity determining region of an H chain consisting of the polypeptide of (a) or (b) below and a complementarity determining region of an L chain consisting of the polypeptide of (c) or (d) below:
(a) a polypeptide consisting of the amino acid sequence as shown in SEQ ID NOs: 1 to 3;
(b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR;
(c) a polypeptide consisting of the amino acid sequence as shown in SEQ ID NOs: 4 to 6;
(d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR;
(15) The human antibody of any one of (1) to (13) which comprises a complementarity determining region of an H chain consisting of the polypeptide of (e) or (f) below and a complementarity determining region of an L chain consisting of the polypeptide of (g) or (h) below:
(e) a polypeptide consisting of the amino acid sequence as shown in SEQ ID NOs: 7 to 9;
(f) a polypeptide which consists of the amino acid sequence as shown in SEQ ID NOs: 7 to 9 wherein one or several amino acid residue(s) is/are substituted, deleted, inserted and/or added and which can be a complementarity determining region of an H chain to TTR;
(g) a polypeptide consisting of the amino acid sequence as shown in SEQ ID NOs: 10 to 12;
(h) a polypeptide which consists of the amino acid sequence as shown in SEQ ID NOs: 10 to 12 wherein one or several amino acid residue(s) is/are substituted, deleted, inserted and/or added and which can be a complementarity determining region of an L chain to TTR;
(16) The human antibody of any one of (1) to (13) which comprises an H chain variable region consisting of the polypeptide of (i) or (j) below and an L chain variable region consisting of the polypeptide of (k) or (l) below:
(i) a polypeptide consisting of the amino acid sequence as shown in SEQ ID NO: 13;
(j) a polypeptide which consists of the amino acid sequence as shown in SEQ ID NO: 13 wherein one or several amino acid residue(s) is/are substituted, deleted, inserted and/or added and which can be an H chain variable region to TTR;
(k) a polypeptide consisting of the amino acid sequence as shown in SEQ ID NO: 14;
(l) a polypeptide which consists of the amino acid sequence as shown in SEQ ID NO: 14 wherein one or several amino acid residue(s) is/are substituted, deleted, inserted and/or added and which can be of an L chain variable region to TTR;
(17) The human antibody of any one of (1) to (13) which comprises an H chain variable region consisting of the polypeptide of (m) or (n) below and an L chain variable region consisting of the polypeptide of (o) or (p) below:
(m) a polypeptide consisting of the amino acid sequence as shown in SEQ ID NO: 15;
(n) a polypeptide which consists of the amino acid sequence as shown in SEQ ID NO: 15 wherein one or several amino acid residue(s) is/are substituted, deleted, inserted and/or added and which can be an H chain variable region to TTR;
(o) a polypeptide consisting of the amino acid sequence as shown in SEQ ID NO: 16;
(p) a polypeptide which consists of the amino acid sequence as shown in SEQ ID NO: 16 wherein one or several amino acid residue(s) is/are substituted, deleted, inserted and/or added and which can be an L chain variable region to TTR;
(18) An H chain variable region fragment comprising a complementarity determining region of an H chain consisting of the polypeptide of (a) or (b) below:
  (a) a polypeptide consisting of the amino acid sequence as shown in SEQ ID NOs: 1 to 3;
  (b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR;
(19) An L chain variable region fragment comprising a complementarity determining region of an L chain consisting of the polypeptide of (c) or (d) below:
  (c) a polypeptide consisting of the amino acid sequence as shown in SEQ ID NOs: 4 to 6;
  (d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR;
(20) An H chain variable region fragment consisting of the polypeptide of (i) or (j) below:
  (i) a polypeptide consisting of the amino acid sequence as shown in SEQ ID NO: 13;
  (j) a polypeptide which consists of the amino acid sequence as shown in SEQ ID NO: 13 wherein one or several amino acid residue(s) is/are substituted, deleted, inserted and/or added and which can be an H chain variable region to TTR;
(21) An L chain variable region fragment consisting of the polypeptide of (k) or (l) below:
  (k) a polypeptide consisting of the amino acid sequence as shown in SEQ ID NO: 14;
  (l) a polypeptide which consists of the amino acid sequence as shown in SEQ ID NO: 14 wherein one or several amino acid residue(s) is/are substituted, deleted, inserted and/or added and which can be an L chain variable region to TTR;
(22) An H chain variable region fragment comprising a complementarity determining region of an H chain consisting of the polypeptide of (e) or (f) below:
  (e) a polypeptide consisting of the amino acid sequence as shown in SEQ ID NOs: 7 to 9;
  (f) a polypeptide which consists of the amino acid sequence as shown in SEQ ID NOs: 7 to 9 wherein one or several amino acid residue(s) is/are substituted, deleted, inserted and/or added and which can be a complementarity determining region of an H chain to TTR;
(23) An L chain variable region fragment comprising a complementarity determining region of an L chain consisting of the polypeptide of (g) or (h) below:
  (g) a polypeptide consisting of the amino acid sequence as shown in SEQ ID NOs: 10 to 12;
  (h) a polypeptide which consists of the amino acid sequence as shown in SEQ ID NOs: 10 to 12 wherein one or several amino acid residue(s) is/are substituted, deleted, inserted and/or added and which can be a complementarity determining region of an L chain to TTR;
(24) An H chain variable region fragment consisting of the polypeptide of (m) or (n) below:
  (m) a polypeptide consisting of the amino acid sequence as shown in SEQ ID NO: 15;
  (n) a polypeptide which consists of the amino acid sequence as shown in SEQ ID NO: 15 wherein one or several amino acid residue(s) is/are substituted, deleted, inserted and/or added and which can be an H chain variable region to TTR;
(25) An L chain variable region fragment consisting of the polypeptide of (o) or (p) below:
  (o) a polypeptide consisting of the amino acid sequence as shown in SEQ ID NO: 16;
  (p) a polypeptide which consists of the amino acid sequence as shown in SEQ ID NO: 16 wherein one or several amino acid residue(s) is/are substituted, deleted, inserted and/or added and which can be an L chain variable region to TTR;
(26) A single-chain variable region fragment of an antibody to TTR, which is formed by linking the H chain variable region fragment comprising a complementarity determining region of an H chain of (18) or the H chain variable region fragment of (20) and the L chain variable region fragment comprising a complementarity determining region of an L chain of (19) or the L chain variable region fragment of (21);
(27) The human antibody of any one of (1) to (13) or a fragment thereof, which is formed by linking a human-derived constant region to the H chain variable region fragment comprising a complementarity determining region of an H chain of (18) or the H chain variable region fragment of (20) and/or to the L chain variable region fragment comprising a complementarity determining region of an L chain of (19) or the L chain variable region fragment of (21);
(28) A single-chain variable region fragment of an antibody to TTR, which is formed by linking the H chain variable region fragment comprising a complementarity determining region of an H chain of (22) or the H chain variable region fragment of (24) and the L chain variable region fragment comprising a complementarity determining region of an L chain of (23) or the L chain variable region fragment of (25);
(29) The human antibody of any one of (1) to (13) or a fragment thereof, which is formed by linking a human-derived constant region to the H chain variable region fragment comprising a complementarity determining region of an H chain of (22) or the H chain variable region fragment of (24) and/or to the L chain variable region fragment comprising a complementarity determining region of an L chain of (23) or the L chain variable region fragment of (25);
(30) A gene coding for the antibody or a fragment thereof of any one of (1) to (29);
(31) A recombinant expression vector comprising the gene of (30);
(32) A transformant wherein the gene of (30) or the expression vector of (31) is introduced;
(33) An apparatus for detecting TTR amyloid comprising the antibody or a fragment thereof of any one of (1) to (29);
(34) A reagent for detecting TTR amyloid comprising the antibody or a fragment thereof of any one of (1) to (29);
(35) A carrier for removing TTR amyloid comprising the antibody or a fragment thereof of any one of (1) to (29);
(36) A diagnostic agent for TTR amyloidosis comprising the antibody or a fragment thereof of any one of (1) to (29);
(37) The diagnostic agent of (36) wherein the TTR amyloidosis is FAP;
(38) The diagnostic agent of (36) wherein the TTR amyloidosis is SSA;
(39) A TTR-fibrillization inhibitor comprising the antibody or a fragment thereof of any one of (1) to (29);
(40) A pharmaceutical composition for the prevention and/or the treatment of TTR amyloidosis comprising the antibody or a fragment thereof of any one of (1) to (29);

(41) The pharmaceutical composition of (40) wherein the TTR amyloidosis is FAP;

(42) The pharmaceutical composition of (40) wherein the TTR amyloidosis is SSA;

(43) A method for measuring the activity to inhibit TTR-fibrillization which comprises a step of reacting a variant TTR with a sample to be tested in the presence of Na deoxycholate;

(44) The method of (43) wherein fibrillization is let to proceed under neutral conditions;

(45) The method of (43) or (44) wherein the concentration of Na deoxycholate is from 0.1% to 1%;

(46) The method of any one of (43) to (45) wherein the sample to be tested is an antibody to TTR;

(47) The method of any one of (43) to (46) wherein the variant TTR is V30M TTR.

Effects of the Invention

The present inventors have created a monoclonal antibody that specifically recognizes TTRs with structural change and succeeded in opening up a path to development of an antibody drug that enables the treatment of FAP. The antibody of the present invention effectively suppresses formation of amyloid fibril and its deposition to tissues by TTR but does not react with normal TTR functioning in blood. Thus, the antibody of the present invention is expected to be an antibody drug excellent in safety. Besides, as an action mechanism, two distinct effects can be expected: (1) formation of amyloid and its deposition to tissues by TTR are suppressed; and (2) TTR amyloid deposited to tissues is also affected to accelerate its clearance, i.e. accumulated amyloid is decreased. These effects can never be attained by the prior art or previous development articles. Therefore, the antibody therapy of the present invention is greatly expected as a novel therapeutic strategy to TTR amyloidosis.

As described above, the antibody of the present invention is not only expected to provide a novel therapeutic method other than liver transplantation to FAP but also has the possibility for use as a therapeutic agent for Senile Systemic Amyloidosis (SSA). For TTR amyloidosis, not only FAP caused by genetic mutation of TTR but also SSA caused by amyloid deposition formed by wild-type TTR chiefly at the heart are known. It is regarded as Alzheimer disease in the heart. Amyloid deposition is also seen in the lung, the vascular wall, the renal medulla and the like. Patients often complain no symptom or symptoms in the heart (indolent heart failure) and sometimes carpal tunnel syndrome. The onset of the disease is observed from the 60's onward and it is said that the onset is observed in approximately one in four people of 80's. In the U.S. alone, an estimated number of more than 400,000 patients is reported. No effective therapeutic method for this disease has been established. The antibody of the present invention, as having the activity to inhibit fibrillization of wild-type TTR, is expected to be applied to SSA.

The antibody product of the present invention is expected to be applied not only to FAP but also to amyloidogenetic diseases in various organs caused by TTR and thus is expected to make a contribution to therapy of patients of these many diseases where a therapeutic method has not yet been found up till the present.

BEST MODE FOR CARRYING OUT THE INVENTION

Figure 1:
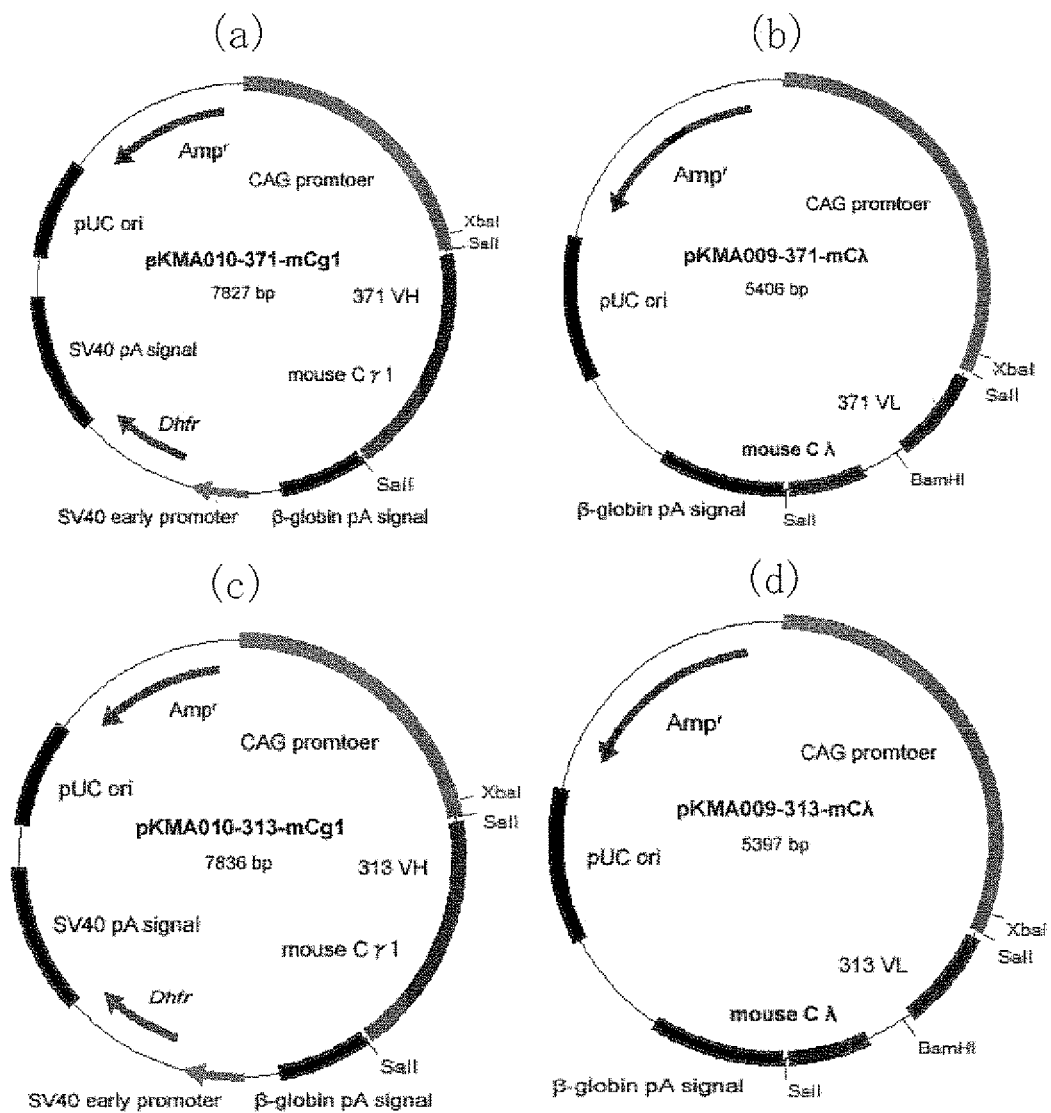
FIG. 1 shows maps of (a) chimeric 371 antibody H chain expression vector pKMA010-371-mCg1, (b) chimeric 371 antibody L chain expression vector pKMA009-371-mCλ, (c) chimeric 313 antibody H chain expression vector pKMA010-313-mCg1, and (d) chimeric 313 antibody L chain expression vector pKMA009-313-mCλ.

The specific embodiments of the present invention are explained hereinbelow. The present invention is not construed to be limited to these embodiments.

1. Recombinant Human Antibody of the Present Invention and a Fragment Thereof

In accordance with the present invention, for obtaining a human antibody that specifically binds to TTRs with structural change and inhibits TTR-fibrillization, focusing on TTR S112I which undergoes structural change and exists in a dimer, S112I was selected as an antigen for preparing an antibody and phage display was used for preparing a human antibody. Technique for preparing an antibody with phage display includes "Phage Display of Peptides and Proteins: A Laboratory Manual Edited by Brian K. Kay et al", "Antibody Engineering: A PRACTICAL APPROACH Edited by J. McCAFFERTY et al", and "ANTIBODY ENGINEERING second edition edited by Carl A. K. BORREBAECK". In accordance with the present invention, S112I fibrillized by acid treatment is immobilized on a plate for panning and then reacted with phage library. For the acid treatment, temperature, time, and pH may suitably be selected for fibrillization of S112I. The presence or absence of fibrillization may be checked by ThioflavinT assay. For instance, S112I may be treated under conditions of pH 3.0 to pH 4.4 at 37° C. for 16 hours. The plate is washed to remove unbound phages and then phages bound to the target molecule are collected and infected to E. coli. After E. coli is cultured, the phages are collected and reacted again with the plate. After performing such a series of panning cycles three to five times, those phages which show excellent reactivity with S112I are selected by ELISA test.

From E. coli producing the selected phages, plasmid DNAs from the phages are collected and nucleotide sequences of VH region (or VL region) are analyzed. The nucleotide sequence of VH region or VL region is inserted into an expression vector containing a nucleotide sequence coding for H chain or L chain constant region to prepare an expression vector of H chain or L chain. The resulting expression vector is introduced into a suitable host (animal cell) and a human antibody is expressed using the host.

In accordance with the present invention, two kinds of human antibodies with different amino acid sequences of CDRs were obtained and the amino acid sequences of framework region of these antibodies were mutated to prepare improved human antibodies (371M, 313M).

A method for analyzing an epitope for a human antibody is illustrated. With a peptide of an amino acid sequence of positions 76-93 of human TTR where one amino acid residue is altered to alanine (the amino acid residue at position 91 is alanine and thus is altered to serine), modified human TTRs are prepared. Conventional site-directed mutagenesis is used to prepare genes of the modified TTRs. The genes are inserted into an expression vector and then expressed and purified with a suitable host (preferably *E. coli*). With conventional Western blotting, the modified TTRs are electrophoresed on SDS-PAGE and are reacted with an antibody of the analysis object to detect reactivity between the variants and the antibody. When modified TTRs with reduced binding to the antibody are found, the modified portion may be considered to be an epitope. The antibody of the present invention has an epitope at positions 78-89 which is presumed to be present in a hidden portion of wild-type TTR tetramer. This epitope was a novel epitope.

The above human antibody may be subject to tests for the specific reactivity to TTRs with structural change, the reactivity with fibrillized TTR, immunostaining to tissues derived from TTR patients, the inhibitory activity to fibrillization by variant TTR, the promoting activity to the macrophage phagocytic ability to TTR amyloid, and the drug efficacy evaluation using FAP animal model.

A method for analyzing specific reactivity to TTRs with structural change includes a method using surface plasmon resonance. Wild-type TTR tetramer, variant TTR (V30M etc.) tetramer, or variant TTR amyloid are prepared. A method for preparing wild-type TTR tetramer and variant TTR tetramer includes a method of Matsubara et al. (Non-patent reference 13). A method for preparing variant TTR amyloid includes acid treatment as described above. Next, these preparations are let to bind to sensor chips, to which an antibody of the analysis object is added for reaction with the sensor chips, thereby indicating the binding of TTR with the antibody as response unit (RU). Here, those antibodies that have RU for variant TTR amyloid significantly higher than RU for wild-type TTR tetramer and variant TTR tetramer are thought to specifically recognize TTRs with structural change. As compared to such tetrameric TTRs, an antibody that specifically recognizes TTRs with a bigger size of molecular structure than tetramer (e.g. TTR amyloid) may also be regarded as an antibody that specifically recognizes TTRs with structural change.

A method for analyzing the activity to inhibit TTR-fibrillization is exemplified below. A solution containing TTR and an antibody to be evaluated is mixed with a surfactant at a final concentration of 0.01-1% and left to stand at such a temperature for such a period of time that allows for TTR to form fibril. Fluorescence intensity is measured by ThioflavinT assay (excitation wavelength 440 nm, fluorescent wavelength 480 nm) to evaluate a degree of TTR-fibrillization. A surfactant includes benzalkonium chloride, sodium deoxycholate, Zwittergent3-16 and NP-40. Most preferable is deoxycholate. A final concentration includes 0.01-1%, and is most preferably 0.1%. Time and temperature includes at 37° C. for 3 to 4 days but may suitably be arranged for their combination. This method of analysis is an excellent evaluation system where denaturation of an antibody to be evaluated may be prohibited since the analysis can be performed at pH close to neutrality.

A method for analyzing the macrophage phagocytic ability to TTR amyloid is exemplified below. Human iPS cells are prepared from skin tissue from healthy adults by the conventional method and are further differentiated to macrophages by the conventional method. TTR fibril and $5 \times 10^4$ cells of the differentiated macrophages are mixed together. An antibody to be evaluated is added and the mixture is cultured for a fixed period of time (e.g. 3 days). A residual quantity of TTR after culture is measured by ELISA to evaluate the phagocytic ability of macrophage.

A method for analyzing the reactivity between the human antibody of the present invention and TTR amyloid is exemplified below. Wild-type TTR and variant TTR are treated under acidic conditions for a period of time sufficient for TTR-fibrillization to prepare TTR amyloid. Time for fibrillization may suitably be selected depending on pH or the kinds of TTR. The samples after the acid treatment are electrophoresed on Native PAGE and subject to silver staining. A broad band at a higher position than 60 kDa may be an index for TTR-fibrillization. Using the conventional Western blotting, the TTR amyloid is electrophoresed on SDS-PAGE and antibodies of analysis object are reacted thereto for detection. An antibody that has a higher reactivity with TTR amyloid as compared to TTR with no acid treatment (TTR not subject to fibrillization) may be regarded as an antibody having the binding activity to TTR amyloid.

A method for the drug efficacy evaluation using FAP animal model is exemplified below. Using V30M Tg rat (Non-patent reference 14; transgenic rat where a gene of human TTR with mutation of valine at position 30 to methionine in the amino acid sequence of TTR is introduced), a fixed amount (e.g. 10 mg/kg) of an antibody to be evaluated is administered for a fixed period of time (e.g. for 6 months) at a fixed frequency (e.g. once per week). After administration, the large intestine is taken out by autopsy and formalin fixed. The fixed tissue of the large intestine is embedded in a paraffin block to prepare tissue section. The tissue section is subject to immunostaining using Polyclonal Rabbit Anti-Human Prealbumin (Dako), HRP-labelled Goat anti-Rabbit IgG (Dako) and a degree of TTR deposition in the muscular layer of the large intestine is digitized and compared between the groups.

The human antibody of the present invention has the inhibitory activity to TTR-fibrillization, the specific binding activity to TTRs with structural change, the effect of promoting the phagocytic ability of macrophage to TTR amyloid, the binding activity to TTR amyloid, and the effect to FAP animal model. As a result of analysis of an epitope for the antibody of the present invention, it was present at TTR78-89. Thus, the present invention includes the human antibodies as follows:

(1) A human antibody having the activity to inhibit fibrillization of TTR;
(2) A human antibody which specifically recognizes TTRs with structural change and does not recognize tetrameric functional TTR;
(3) A human antibody which specifically binds to TTR amyloid;
(4) A human antibody which promotes removal of TTR amyloid;
(5) A human antibody which promotes the phagocytic ability of macrophages to TTR amyloid;
(6) A human antibody which has a therapeutic effect and/or a preventive effect to TTR amyloidosis;
(7) A human antibody which has an epitope of TTR78-89.

The antibodies of (1) to (7) above may have one characteristic feature as shown in each of (1) to (7) or may have a combination of characteristic features as shown in (1) to (7).

For the human antibody (371M) of the present invention, the amino acid and nucleotide sequences of CDR1-3 of VH region or VL region are shown in the following table.

| VH region | CDR1 | SYAMS | SEQ ID NO: 1 |
|---|---|---|---|
| | | agctatgccatgagc | SEQ ID NO: 26 |
| | CDR2 | AISGSGGSTYYADSVKG | SEQ ID NO: 2 |
| | | gctattagtggtagtggtggtagcacatac tacgcagactccgtgaagggc | SEQ ID NO: 27 |
| | CD3 | GTRTNWYFDL | SEQ ID NO: 3 |
| | | gggacccggacgaactggtacttcgatctc | SEQ ID NO: 28 |
| VL region | CDR1 | SGSRSNIGSNTVN | SEQ ID NO: 4 |
| | | tctggaagtagatccaacatcgggagtaat actgttaac | SEQ ID NO: 29 |
| | CDR2 | SNNQRPS | SEQ ID NO: 5 |
| | | agtaataatcagcggccctca | SEQ ID NO: 30 |
| | CDR3 | AAWDDSLYGPV | SEQ ID NO: 6 |
| | | gcagcatgggatgacagtctgtatggtcct gtg | SEQ ID NO: 31 |

Thus, the present invention includes the human antibody having the following characteristic features of the amino acid sequence:

(8) A human antibody which comprises a complementarity determining region of an H chain consisting of the polypeptide of (a) or (b) below and a complementarity determining region of an L chain consisting of the polypeptide of (c) or (d) below:

(a) a polypeptide consisting of the amino acid sequence as shown in SEQ ID NOs: 1 to 3;

(b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR;

(c) a polypeptide consisting of the amino acid sequence as shown in SEQ ID NOs: 4 to 6;

(d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR.

The above antibody may also have characteristic features as shown in each of (1) to (7).

For the human antibody (313M) of the present invention, the amino acid and nucleotide sequences of CDR1-3 of VH region or VL region are shown in the following table.

Thus, the present invention includes the human antibody having the following characteristic features of the amino acid sequence:

(9) A human antibody which comprises a complementarity determining region of an H chain consisting of the polypeptide of (e) or (f) below and a complementarity determining region of an L chain consisting of the polypeptide of (g) or (h) below:

(e) a polypeptide consisting of the amino acid sequence as shown in SEQ ID NOs: 7 to 9;

(f) a polypeptide which consists of the amino acid sequence as shown in SEQ ID NOs: 7 to 9 wherein one or several amino acid residue(s) is/are substituted, deleted, inserted and/or added and which can be a complementarity determining region of an H chain to TTR;

(g) a polypeptide consisting of the amino acid sequence as shown in SEQ ID NOs: 10 to 12;

(h) a polypeptide which consists of the amino acid sequence as shown in SEQ ID NOs: 10 to 12 wherein one or several amino acid residue(s) is/are substituted, deleted, inserted and/or added and which can be a complementarity determining region of an L chain to TTR.

The above antibody may also have characteristic features as shown in each of (1) to (7).

For the human antibody (371M), the amino acid and nucleotide sequences of VH region or VL region are shown in the following table.

TABLE 2

| VH region | CDR1 | SYYMH | SEQ ID NO: 7 |
|---|---|---|---|
| | | agctactatatgcac | SEQ ID NO: 32 |
| | CDR2 | IINPSGGSTSYAQKFQG | SEQ ID NO: 8 |
| | | ataatcaaccctagtggtggtagcacaagc tacgcacagaagttccagggc | SEQ ID NO: 33 |
| | CDR3 | FGSSSRGNDAFDI | SEQ ID NO: 9 |
| | | ttcgggtcttctagcagggggaatgatgct tttgatatc | SEQ ID NO: 34 |
| VL region | CDR1 | SGDVLAKKYAR | SEQ ID NO: 10 |
| | | tcaggagatgtactggcaaaaaaatatgct cgg | SEQ ID NO: 35 |
| | CDR2 | KDSERPS | SEQ ID NO: 11 |
| | | aaagacagtgagcggccctca | SEQ ID NO: 36 |
| | CDR3 | YSAADNKEAV | SEQ ID NO: 12 |
| | | tactctgcggctgacaacaaggaggctgtg | SEQ ID NO: 37 |

TABLE 3

| VH region | EVQLVESGGGVVQPGGSLRLSCAASGFTFSSYAMSWVRQA PGKGLEWVSAISGSGGSTYYADSVKGRFTISRDNSKNTLY LQMNSLRAEDTAVYYCAKGTRTNWYFDLWGRGTLVTVSS | SEQ ID NO: 13 |
|---|---|---|
| | gaggtgcagctggtggagtccgggggaggcgtggtccagc ctggggggtccctgagactctcctgtgcagcctctggatt cacctttagcagctatgccatgagatgggtccgccaggct ccagggaaggggctggagtgggtctcagetattagtggta gtggtggtageacatactacgcagactcegtgaagggccg gttcaccatctccagagacaattccaagaacacgctgtat ctgcaaatgaacagcctgagagccgaggacacggccgtat attactgtgcgaaagggacccggacgaactggtacttcga tctctggggccgtggcaccctggtcaccgtctcctca | SEQ ID NO: 38 |
| VL region | SYELTQPPSASGTPGQRVTISCSGSRSNIGSNTVNWYQQV PGTAPKLLIYSNNQRPSGVPDRFSGSKSGTSASLAISGLQ SEDEAEYYCAAWDDSLYGPVFGGGTQLTVL | SEQ ID NO: 14 |
| | tcctatgagctgacacagccaccctcagcgtctgggaccc ccgggcagagggtcaccatctcttgttctggaagtagatc caacatcgggagtaatactgttaactggtaccaacaggtc ccaggaacggcccccaaactcctcatttatagtaataatc agcggccctcaggggtccctgaccgattctctggctccaa gtctggcacctcagcctccctggcatcagtggactccag tctgaggatgaggctgaatattattgtgcagcatgggatg acagtctgtatagtcctgtgttcggaggaggcacccagct gaccgtccta | SEQ ID NO: 39 |

Thus, the present invention includes the human antibody having the following characteristic features of the amino acid sequence:

(10) A human antibody which comprises an H chain variable region consisting of the polypeptide of (i) or (j) below and an L chain variable region consisting of the polypeptide of (k) or (l) below:
(i) a polypeptide consisting of the amino acid sequence as shown in SEQ ID NO: 13;
(j) a polypeptide which consists of the amino acid sequence as shown in SEQ ID NO: 13 wherein one or several amino acid residue(s) is/are substituted, deleted, inserted and/or added and which can be a complementarity determining region of an H chain to TTR;
(k) a polypeptide consisting of the amino acid sequence as shown in SEQ ID NO: 14;
(l) a polypeptide which consists of the amino acid sequence as shown in SEQ ID NO: 14 wherein one or several amino acid residue(s) is/are substituted, deleted, inserted and/or added and which can be a complementarity determining region of an L chain to TTR.

The above antibody may also have characteristic features as shown in each of (1) to (7).

For the human antibody (313M), the amino acid and nucleotide sequences of VH region or VL region are shown in the following table.

TABLE 4

| VH region | QVQLVQSGAEVHKPGASVKVSCKASGYIFTSYYMHWVRQAP GQGLEWMGIINPSGGSTSYAQKFQGRVTMTRDTSTSTVYME LSSLRSEDTAVYYCASFGSSSRGNDAFDIWGQGTMVTVSS | SEQ ID NO: 15 |
|---|---|---|
| | caggtccagctggtacagtctggggctgaggtgaagaagcc tggggcctcagtgaaggtttcctgcaaggcatctggataca ccttcaccagctactatatgcactgggtgcgacaggcccct ggacaagggcttgagtggatgggaataatcaacccctagtgg tggtagcacaagctacacacagaagttccagggcagagtca ccatgaccagggacacgtccacgagcacagtctacatggag ctgagcagcctgagatctgaggacacggccgtgtattactg tgcgagtttcgggtcttctagcaggggaatgatgcttttg atatctggggccaagggacaatggtcaccgtctattca | SEQ ID NO: 40 |
| VL region | SYELTQPSSVSVSPGQTARITCSGDVLAKKYARWFQQKPGQ APVLVIYKDSERPSGIPERFSGSSSGTTVTLTISGAQVEDE ADYYCYSAADNKEAVFGGGTQLTVL | SEQ ID NO: 16 |
| | tcctatgagctgacacagccatcctcagtgtcagtgtctcc gggacagacagccaggatcacctgctcaggagatgtactgg caaaaaaatatgctcggtggttccaacagaagccaggccag gcccctgtgctggtgatttataaagacagtgagcggccctc agggatccctgagcgattctcaggctccagctcagggacca cagtcaccttgaccatcagcggggcccaggttgaggatgag gctgactattactgttactctgcggctgacaacaaggaggc tgtgttaggaggaggcacccagctgaccgtccta | SEQ ID NO: 41 |

Thus, the present invention includes the human antibody having the following characteristic features of the amino acid sequence:

(11) A human antibody which comprises an H chain variable region consisting of the polypeptide of (m) or (n) below and an L chain variable region consisting of the polypeptide of (o) or (p) below:
  (m) a polypeptide consisting of the amino acid sequence as shown in SEQ ID NO: 15;
  (n) a polypeptide which consists of the amino acid sequence as shown in SEQ ID NO: 15 wherein one or several amino acid residue(s) is/are substituted, deleted, inserted and/or added and which can be a complementarity determining region of an H chain to TTR;
  (o) a polypeptide consisting of the amino acid sequence as shown in SEQ ID NO: 16;
  (p) a polypeptide which consists of the amino acid sequence as shown in SEQ ID NO: 16 wherein one or several amino acid residue(s) is/are substituted, deleted, inserted and/or added and which can be a complementarity determining region of an L chain to TTR.

The above antibody may also have characteristic features as shown in each of (1) to (7).

The present invention includes the H chain variable region fragment comprising the following CDR of H chain:

(12) An H chain variable region fragment comprising a complementarity determining region of an H chain consisting of the polypeptide of (a) or (b) below:
  (a) a polypeptide consisting of the amino acid sequence as shown in SEQ ID NOs: 1 to 3;
  (b) a polypeptide which consists of the amino acid sequence as shown in SEQ ID NOs: 1 to 3 wherein one or several amino acid residue(s) is/are substituted, deleted, inserted and/or added and which can be a complementarity determining region of an H chain to TTR.

(13) An H chain variable region fragment comprising a complementarity determining region of an H chain consisting of the polypeptide of (e) or (f) below:
  (e) a polypeptide consisting of the amino acid sequence as shown in SEQ ID NOs: 7 to 9;
  (f) a polypeptide which consists of the amino acid sequence as shown in SEQ ID NOs: 7 to 9 wherein one or several amino acid residue(s) is/are substituted, deleted, inserted and/or added and which can be a complementarity determining region of an H chain to TTR.

The present invention includes the L chain variable region fragment comprising the following CDR of L chain:

(14) An L chain variable region fragment comprising a complementarity determining region of an L chain consisting of the polypeptide of (c) or (d) below:
  (c) a polypeptide consisting of the amino acid sequence as shown in SEQ ID NOs: 4 to 6;
  (d) a polypeptide which consists of the amino acid sequence as shown in SEQ ID NOs: 4 to 6 wherein one or several amino acid residue(s) is/are substituted, deleted, inserted and/or added and which can be a complementarity determining region of an L chain to TTR.

(15) An L chain variable region fragment comprising a complementarity determining region of an L chain consisting of the polypeptide of (g) or (h) below:
  (g) a polypeptide consisting of the amino acid sequence as shown in SEQ ID NOs: 10 to 12;
  (h) a polypeptide which consists of the amino acid sequence as shown in SEQ ID NOs: 10 to 12 wherein one or several amino acid residue(s) is/are substituted, deleted, inserted and/or added and which can be a complementarity determining region of an L chain to TTR.

The present invention includes the following H chain variable region fragment:

(16) An H chain variable region fragment consisting of the polypeptide of (i) or (j) below:
  (i) a polypeptide consisting of the amino acid sequence as shown in SEQ ID NO: 13;
  (j) a polypeptide which consists of the amino acid sequence as shown in SEQ ID NO: 13 wherein one or several amino acid residue(s) is/are substituted, deleted, inserted and/or added and which can be a complementarity determining region of an H chain to TTR.

(17) An H chain variable region fragment consisting of the polypeptide of (m) or (n) below:
  (m) a polypeptide consisting of the amino acid sequence as shown in SEQ ID NO: 15;
  (n) a polypeptide which consists of the amino acid sequence as shown in SEQ ID NO: 15 wherein one or several amino acid residue(s) is/are substituted, deleted, inserted and/or added and which can be a complementarity determining region of an H chain to TTR.

The present invention includes the following L chain variable region fragment:

(18) An L chain variable region fragment consisting of the polypeptide of (k) or (l) below:
  (k) a polypeptide consisting of the amino acid sequence as shown in SEQ ID NO: 14;
  (l) a polypeptide which consists of the amino acid sequence as shown in SEQ ID NO: 14 wherein one or several amino acid residue(s) is/are substituted, deleted, inserted and/or added and which can be a complementarity determining region of an L chain to TTR.

(19) An L chain variable region fragment consisting of the polypeptide of (o) or (p) below:
  (o) a polypeptide consisting of the amino acid sequence as shown in SEQ ID NO: 16;
  (p) a polypeptide which consists of the amino acid sequence as shown in SEQ ID NO: 16 wherein one or several amino acid residue(s) is/are substituted, deleted, inserted and/or added and which can be a complementarity determining region of an L chain to TTR.

The present invention includes the following single-chain variable region fragment:

(20) A single-chain variable region fragment of an antibody to TTR, which is formed by linking the H chain variable region fragment comprising a complementarity determining region of an H chain of (12) or the H chain variable region fragment of (16) and the L chain variable region fragment comprising a complementarity determining region of an L chain of (14) or the L chain variable region fragment of (18).

(21) A single-chain variable region fragment of an antibody to TTR, which is formed by linking the H chain variable region fragment comprising a complementarity determining region of an H chain of (13) or the H chain variable region fragment of (17) and the L chain variable region fragment comprising a complementarity determining region of an L chain of (15) or the L chain variable region fragment of (19).

For a single-chain variable region fragment, an H chain variable region fragment and an L chain variable region fragment are usually linked to each other via a suitable peptide linker and the like. For the peptide linker, any single-chain peptide consisting of e.g. 10 to 25 amino acid residues is used.

The present invention includes the following antibody or a fragment thereof, which is formed by linking a human-derived constant region to the H chain variable region fragment and/or to the L chain variable region fragment:

(22) A human antibody or a fragment thereof, which is formed by linking a human-derived constant region to the H chain variable region fragment comprising a complementarity determining region of an H chain of (12) or the H chain variable region fragment of (16) and/or to the L chain variable region fragment comprising a complementarity determining region of an L chain of (14) or the L chain variable region fragment of (18).

(23) A human antibody or a fragment thereof, which is formed by linking a human-derived constant region to the H chain variable region fragment comprising a complementarity determining region of an H chain of (13) or the H chain variable region fragment of (17) and/or to the L chain variable region fragment comprising a complementarity determining region of an L chain of (15) or the L chain variable region fragment of (19).

The above antibody or a fragment thereof where a human-derived constant region is bound may be Fab, Fab', F(ab')$_2$, scAb having at least a portion of Fc region, or scFvFc, or even a complete antibody. As used herein, scAb is that which is formed by linking a portion of domain (c domain) of L chain or H chain constant region to scFv whereas scFvFc is that which is formed by linking a portion of constant region of H chain (Fc region) to scFv.

The antibody as mentioned above also includes a protein structurally relevant to an antibody and refers to an immunoglobulin. Besides, the antibody of the present invention may be of any class of IgA, IgD, IgE, IgG or IgM. In other words, the antibody of the present invention may be a monomer or a polymer such as a dimer, a trimer, a tetramer or a pentamer.

As used herein, the phrase "wherein one or several amino acid residue(s) is/are substituted, deleted, inserted and/or added" means that such a number of amino acid residue(s) that can afford to substitution, deletion, insertion and/or addition is/are substituted, deleted, inserted and/or added by a known method for preparing a mutant protein such as site-directed mutagenesis. Thus, for instance, the above polypeptide (b) is a mutant peptide of the above polypeptide (a). As used herein, the term "mutation" means principally mutation artificially introduced by a known method for preparing a mutant protein but may also be the similar mutant protein which is present in nature (e.g. human) and isolated and purified.

The "mutation", when the antibody of the present invention or a fragment thereof is used as a pharmaceutical composition (i.e. administered to human), is done within such a range that a human-derived structure or human does not induce immune reaction and, when the antibody of the present invention or a fragment thereof is used as a detection device or a diagnostic agent (i.e. not administered to human), is not particularly limited. Besides, when the antibody of the present invention or a fragment thereof is administered to human, mutation is performed preferably within such a range that a higher order structure of CDR recognizing an antigen is maintained.

The antibody of the present invention or a fragment thereof may comprise an additional polypeptide. Such addition of a polypeptide includes epitope labelling of the protein of the present invention with e.g. His, Myc, Flag, etc.

Besides, the antibody of the present invention or a fragment thereof may be bound with a modifier so as to improve its stability or antibody titer. Namely, the antibody of the present invention or a fragment thereof may be a modified antibody. A modifier includes, for instance, a sugar chain, a macromolecule, and the like. When modification is performed with a sugar chain, the sugar chain may possibly have a certain physiological activity. However, when modification is performed with a simple macromolecule such as polyethylene glycol (PEG), the molecule per se does not show a physiological activity. Besides, it is possible that PEGylation suppresses absorption in the liver or improve stability in blood. Thus, a modifier is preferably a simple macromolecule such as PEG.

As is the case with the preparation of a mutant peptide, modification of the antibody of the present invention or a fragment thereof with a modifier, when the antibody of the present invention or a fragment thereof is used as a therapeutic agent, is done within such a range that human does not induce immune reaction and, when the antibody of the present invention or a fragment thereof is used as a detection device or a diagnostic agent, is not particularly limited. Besides, when the antibody of the present invention or a fragment thereof is administered to human, modification is performed preferably within such a range that a higher order structure of CDR recognizing an antigen is maintained.

2. Gene of the Present Invention

The present invention includes a gene coding for the antibody or a fragment thereof of the above item 1. For instance, the present invention includes a gene including the following nucleotide sequences as an open reading frame (ORF) region and a modified gene with these nucleotide sequences partially modified:

(1) nucleotide sequence comprising SEQ ID NOs:1-3 and/or SEQ ID NOs:4-6;
(2) nucleotide sequence comprising SEQ ID NOs:7-9 and/or SEQ ID NOs:10-12;
(3) nucleotide sequence comprising SEQ ID NO:13 and/or SEQ ID NO:14;
(4) nucleotide sequence comprising SEQ ID NO:15 and/or SEQ ID NO:16.

The above gene, coding for the antibody of the present invention or a fragment thereof, may be introduced into a suitable host (e.g. bacteria, yeast) for expression of the antibody of the present invention or a fragment thereof.

Besides, the above gene may be one further comprising an untranslated region (UTR) or a sequence of a vector including an expression vector in addition to a nucleotide sequence coding for the antibody or a fragment thereof. For instance, the sequence of SEQ ID NO: 13 or 14 is linked to a sequence of a vector to form the gene of the present invention. The resultant gene may then be amplified in a suitable host to amplify the gene of the present invention as desired. Also, a portion of the gene of the present invention may be used as a probe.

The gene of the present invention may be utilized as a gene therapy agent in the diseases associated with TTR amyloid. The gene therapy agent may be designed to express the antibody of the present invention or a fragment thereof within the living body after administration thereof so that the antibody of the present invention or a fragment thereof is formed within the living body after ingestion thereof to thereby exhibit the similar effect to that of the above inhibitor.

3. Recombinant Expression Vector of the Present Invention

The present invention includes a recombinant expression vector comprising the gene of the above item 2, i.e. the gene coding for the antibody or a fragment thereof of the above item 1. For instance, the recombinant expression vector of the present invention includes the one where cDNA having the nucleotide sequence of SEQ ID NO: 13 or 14 is inserted. The recombinant expression vector may be prepared with, but not particularly limited to, plasmid, phage, cosmid and the like.

A concrete sort of a vector is not particularly limited but such a vector that allows for expression in a host cell may suitably be selected. Namely, a promoter sequence may suitably be selected so as to ensure gene expression depending on the kind of a host cell and a variety of plasmids etc. into which the promoter and the gene of the present invention are inserted may be used as an expression vector.

A variety of markers may be used for confirming if the gene of the present invention is introduced into a host cell or if the gene of the present invention is surely expressed in a host cell. For instance, a gene deficient in a host cell is used as a marker and plasmid etc. comprising the marker and the gene of the present invention is introduced as an expression vector into a host cell. Thereby, the introduction of the gene of the present invention may be verified by the expression of the marker gene. Alternatively, the antibody of the present invention or a fragment thereof and a marker protein may be expressed as a fusion protein. For instance, Green Fluorescent Protein (GFP) derived from *Aequorea victoria* may be used as a marker and the antibody of the present invention or a fragment thereof may be expressed as a GFP fusion protein.

The above host cell is not particularly limited but a variety of known cells may suitably be used. Specifically, the host cell includes, but not particularly limited to, an animal cell including cells from human or mouse, *Caenorhabditis elegans*, an oocyte of *Xenopas laevis*, a culture cell of a variety of mammals (rat, rabbit, pig, monkey, etc.), a culture cell of insects such as *Drosophila melanogaster* or silkworm moth, bacteria such as *Escherichia coli*, yeast (budding yeast (*Saccharomyces cerevisiae*) and fission yeast (*Schizosaccharomyces pombe*)) and the like.

A method for introducing a recombinant expression vector into a host cell, i.e. a method for transfection, is not particularly limited but the conventional known methods such as electroporation, calcium phosphate method, liposome method and DEAE-dextran method may suitably be used.

A transformant of the present invention is a transformant where the gene of the above item 2, i.e. the gene coding for the antibody or a fragment thereof of the above item 1, is introduced. As used herein, "a gene is introduced" means that a gene is introduced expressibly into a cell of interest (host cell) by known genetic engineering techniques (gene manipulation techniques). The term "transformant" refers to not only a cell, a tissue or an organ but also an animal individual. An animal of interest is not particularly limited but includes mammals such as cow, pig, sheep, goat, rabbit, dog, cat, guinea pig, hamster, mouse and rat. In particular, rodents such as mouse and rat are widely used as an experimental animal and a disease animal model. Among them, mouse is preferable as an experimental animal and a disease animal model since many inbred strains have been created and techniques of culture of fertilized eggs and in vitro fertilization have been completed.

The antibody or a fragment thereof of the above item 1 can be prepared with the transformant of the present invention which is prepared using the expression vector of the present invention.

4. Utilization of Human Antibody of the Present Invention or a Fragment Thereof

The human antibody of the present invention specifically recognizes TTR with structural change (e.g. TTR amyloid), inhibits fibrillization of TTR and exerts the preventive effect against FAP. Thus, the present invention includes a device for detecting structural change of TTR, a diagnostic agent for TTR amyloidosis (in particular, FAP), a medicament for inhibiting fibrillization of TTR, and a pharmaceutical composition for preventing and/or treating TTR amyloidosis (in particular, FAP).

The present invention includes a device for detecting structural change of TTR comprising the antibody of (1) or a fragment thereof (a detection device for TTR amyloid). The detection device of the present invention includes, for instance, an antibody chip or an antibody column etc. in which an antibody that specifically binds to TTR with structural change or a fragment thereof is immobilized on a basement (carrier). The detection device of the present invention, for instance, may be used for detecting TTR with structural change (e.g. TTR amyloid) contained in a sample such as blood or urine. Besides, the detection device of the present invention may also be used for diagnostic or therapeutic application for determining diseases associated with TTR with structural change (e.g. TTR amyloid) or for evaluating the therapeutic effect.

The present invention further includes a carrier used for removal of TTR amyloid comprising the antibody of (1) or a fragment thereof (a carrier for removal of TTR amyloid). This carrier for removal may be prepared by binding by a usual method the antibody and the like to a carrier that is normally used in chromatography. The above carrier for removal is used in such a manner that blood is taken from patients suffering from amyloidosis caused by TTR amyloid and is passed through a column filled up with the carrier for removal to thereby remove TTR amyloid in blood.

Furthermore, the present invention includes a reagent for detecting TTR amyloid comprising the antibody or a fragment thereof of the above item 1 (a reagent for detecting TTR amyloid). Thus, when label immunoassay such as radioimmunoassay, enzyme immunoassay and fluorescent immunoassay is applied, TTR in a test sample can qualitatively or quantitatively be analyzed in a rapid and accurate manner. In the label immunoassay, the above antibody or a fragment thereof is used with a label of e.g. a radioactive substance, an enzyme and/or a fluorescent substance. Besides, the antibody or a fragment thereof specifically reacts with TTR amyloid to show an immune reaction and therefore the measurement of the immune reaction with the labelling substance as an index allows for detection of small quantities of TTR amyloid present in a test sample at high precision. Label immunoassay, as compared to bioassay, is characterized by that a large number of test samples can be analyzed at a time, that time and labor for analysis is small, and that analysis is at high precision.

The present invention includes a diagnostic agent for TTR amyloidosis comprising the antibody or a fragment thereof of the above item 1. A method for diagnosing the disease of the present invention comprises measuring an amount of TTR amyloid in a test sample (blood, body fluid, tissue etc.) and diagnosing the disease in accordance with the results of the measurement. The disease of interest includes the one caused by TTR amyloid, including Senile Systemic Amyloidosis (SSA) and Familial Amyloidotic Polyneuropathy (FAP).

The antibody of the present invention proved to show the effect to suppress fibrillization of TTR. Therefore, the present invention includes a medicament for inhibiting fibrillization of TTR comprising the antibody or a fragment thereof of the above item 1 (a fibrillization inhibitor). The fibrillization inhibitor may contain pharmaceutically acceptable additives such as one or more kinds of excipients, one or more kinds of binding agents, one or more kinds of disintegrating agents, one or more kinds of lubricants and one or more kinds of buffers.

The human antibody of the present invention proved to show the effect when administered to a model animal of TTR amyloidosis. Therefore, the present invention includes a pharmaceutical composition for preventing and/or treating TTR amyloidosis comprising the antibody or a fragment thereof of the above item 1. The pharmaceutical composition may contain pharmaceutically acceptable additives such as one or more kinds of excipients, one or more kinds of binding agents, one or more kinds of disintegrating agents, one or more kinds of lubricants and one or more kinds of buffers.

The present invention is further explained in more detail by means of the following Examples but is not construed to be limited thereto. When the commercially available kits or reagents are used, the experiments were performed in accordance with protocol attached thereto unless otherwise mentioned.

EXAMPLE 1

Preparation of Purified Recombinant S112I TTR

Referring to Matsubara et al. (Non-patent reference 13 and Non-patent reference 15), a purified recombinant TTR was prepared. E. coli strain M15 was transfected with S112I TTR (mutant human TTR where serine at position 112 was altered to isoleucine) expression vector pQE30-hTTR (S112I)-His and cultured with 20 mL of LB/Ampicillin (50 µg/mL)/Kanamycin (25 g/mL) at 37° C. At the point of O.D.600 nm=0.5, IPTG was added at a final concentration of 10 mM and culture was continued overnight. The cells were collected from the culture by centrifugation and suspended in Buffer A (50 mM PB+0.3 M NaCl+10 mM Imidazole+20 mM 2-Mercaptoethanol). The suspension was sonicated for 15 minutes and then centrifuged to collect supernatant. The supernatant was subject to His-tag purification with Ni-NTA Agarose (QIAGEN) and the eluent fraction containing the recombinant TTR was dialyzed against 20 mM $NaHCO_3$. The recombinant TTR after dialysis was purified by gel filtration with Superdex 75 (GE Healthcare) using 10 mM PB (pH7.5) and a fraction of dimeric TTR was used as a purified recombinant TTR S112I.

EXAMPLE 2

Cloning of Human TTR Gene

For constructing a human TTR expression vector, cloning of a human TTR gene was performed. Using Human liver Marathon-Ready cDNA (Clontech) as a template, PCR was conducted using primers (TTR-F2: SEQ ID NO:17 and TTR-R: SEQ ID NO:18), designed at the 5'-end and the 3'-end of mature TTR, and Ex-Taq (Takara). After TA cloning of the PCR products into pCR2.1-TOPO, the nucleotide sequence of a human TTR gene was confirmed by sequence analysis. After confirming that the sequence was correct, pCR2.1-TOPO where the TTR gene was inserted was treated with BamHI and HindIII to cleave a region containing the sequence coding for the TTR gene. The cleaved sequence was introduced into pQE-30 (QIAGEN) previously treated with BamHI and HindIII to construct a wild-type human TTR expression vector.

EXAMPLE 3

Construction of Human TTR Mutant Expression Vector

Using the human TTR expression vector constructed in Example 2 as a template, point mutation of an amino acid was introduced using site-directed mutagenesis. Point mutation of an amino acid was conducted for each of 24 kinds of mutations D18G, V30M, E54K, L55P, Y114C, V122I, K76A, S77A, Y78A, W79A, K80A, A81S, L82A, G83A, I84A, S85A, P86A, F87A, H88A, E89A, H90A, A91A, E92A, and V93A. The sequences coding for the above 24kinds of the TTR mutants were introduced into pQE-30.

EXAMPLE 4

Preparation of Purified Recombinant TTR

E. coli strain M15 was transfected with the expression vectors constructed in Examples 2 and 3 which express the wild-type TTR or D18G, V30M, E54K, L55P, Y114C, Y116S or V122I TTR mutants and purified recombinant TTRs were prepared by the procedures of Example 1. For the above TTR mutants, a tetrameric TTR fraction was used as a purified recombinant TTR.

EXAMPLE 5

Isolation of Anti-human TTR Antibody

An antibody to a human TTR with structural change was isolated by screening scFv phage display library prepared with human VH and VL cDNAs from mRNA from human B cells (e.g. the lymph node and the spleen). The antibody library used is excellent one containing more than $10^{11}$ kinds of various antibody molecules.

The purified S112I TTR mutant prepared in Example 1 was diluted with 10 mM PB (pH 7.5) at 3 mg/mL and mixed with an equivalent amount of 200 mM acetate buffer+100 mM NaCl (pH 4.4) at a concentration of 1.5 mg/mL. The mixture was reacted in an incubator at 37° C. for 16 hours to prepare S112I TTR fibril. For TTR after the reaction, fluorescence intensity was measured by ThioflavinT assay to confirm the progress of fibrillization. ThioflavinT assay was performed by diluting the mixture with 50 mM Glycine-NaOH Buffer (pH 9.5) so that ThioflavinT is 20 µM and TTR is 30-60 µg/mL and measuring fluorescence intensity with a spectral fluorescence photometer FP-6500 (JASCO) (excitation wavelength 440 nm, fluorescent wavelength 480 nm).

S112I TTR fibril was immobilized to Maxisorp plate (Nunc) using the conventional procedures and scFv phages specifically binding to S112I TTR fibril were obtained using the conventional procedures (Antibody Phage Display Methods and protocols Edited by Philippa M. O'Brien and Robert Aitken). The clones of the obtained scFv-phages were named "371" and "313". The binding activity of the obtained scFv phages was evaluated by the method as described below.

EXAMPLE 6

Preparation of Recombinant TTR Fibril

Seven kinds of the purified mutant TTRs D18G, V30M, E54K, L55P, Y114C, Y116S and V122I prepared in Example 4 and the purified wild-type TTR were diluted with 10 mM PB (pH 7.5) at 3 mg/mL and mixed with an equivalent amount of 200 mM acetate buffer+100 mM NaCl (pH 3.0) at a concentration of 1.5 mg/mL. The mixture was reacted in an incubator at 37° C. overnight to prepare TTR fibril. For TTR after the reaction, fibrillization was confirmed by ThioflavinT assay.

EXAMPLE 7

Binding Activity Test of Anti-TTR Antibody

The antibody binding activity of the obtained scFv phages was evaluated by ELISA. The S112I TTR fibril prepared in Example 5 and the V30M TTR fibril prepared in Example 6 were diluted with PBS (SIGMA) at 10 μg/mL. Each 50 μL/well of the diluent was added to Maxisorp Plate (Nunc) and incubated at room temperature for 1 hour to immobilize TTR. Each 300 μL/well of 1% BSA-PBS was added to the immobilized plate and incubated at room temperature for 1 hour for blocking the plate. Each 100 μL of the culture supernatant of the obtained scFv phages was added to each well of the plate and incubated at 37° C. After 1 hour, the well was washed with PBST and each 100 μL of the detection antibody anti-M13/HRP (GE Healthcare) diluted 5000-folds with 1% BSA-PBS was added to each well of the plate and incubated at 37° C. After 1 hour, the well was washed with PBST and each 100 μL of TMB (SIGMA) was added to each well of the plate for development. After 30 minutes, the reaction was quenched with 1N sulfuric acid and color development value (O.D. 450 nm/650 nm) was measured with a microplate reader (Molecular Devices).

As a result, scFv371 and scFv313 were found to have an excellent binding activity to S112I TTR fibril and V30M TTR fibril.

EXAMPLE 8

Sequence Analysis of scFv371 and scFv313

The nucleotide sequences of VH region or VL region of the obtained scFv371 and scFv313 were confirmed. The DNA nucleotide sequences contained in both phages were determined with Big Dye Terminator v3.1 Cycle sequencing kit (Applied Biosystems).

ScFv371 and scFv313 where several amino acid residues were modified in VH region or VL region were designed and constructed and named 371M antibody and 313M antibody, respectively. CDR1-3 in VH region or VL region of 371M and 313M were determined by Kabat numbering. The amino acid sequences and the nucleotide sequences of said CDR1-3 are shown in SEQ ID NOs: 1 to 12. The amino acid sequences and the nucleotide sequences of VH region or VL region are shown in SEQ ID NOs: 13 to 16.

EXAMPLE 9

Expression of Chimeric 371 Antibody and Chimeric 313 Antibody

The V region sequences of the obtained scFv371 and scFv313 were introduced into mouse IgG1λ expression vector and expression of these antibodies having mouse constant regions (hereinafter referred to as "chimeric 371 antibody" and "chimeric 313 antibody") were performed.

Using as a template the plasmids contained in scFv371 and scFv313 phages obtained in Example 5, a region containing VH and VL of scFv371 and scFv313 in the combination as shown in the following table was amplified by PCR. Table 5 shows a combination of primers and SEQ ID NOs.

TABLE 5

| | VH | | VL | |
|---|---|---|---|---|
| | 5'- | 3'- | 5'- | 3'- |
| 371 | 371-VH-Fw SEQ ID NO: 19 | 371-VH-Rv SEQ ID NO: 20 | 371/313-VL-Fw SEQ ID NO: 21 | 371/313-VL-Rv SEQ ID NO: 22 |
| 313 | 313-VH-Fw SEQ ID NO: 23 | 313-VH-Rv SEQ ID NO: 24 | 371/313-VL-Fw SEQ ID NO: 21 | 371/313-VL-Rv SEQ ID NO: 22 |

The amplified sequence of VH region was introduced into the vector pKMA010-mCg1 (previously treated with XhoI and NruI) expressing mouse Cγ1 constant region and the amplified sequence of VL region was introduced into the vector pKMAC009-mCλ (previously treated with XhoI and BamHI) expressing mouse Cλ constant region, using In-fusion enzyme (Clontech) (FIG. 1). pKMA010-371/313-mCg1 vector is such that the VH region of scFv371 or scFv313 and the mouse Cγ1 constant region are inserted downstream CAG promoter and has DHFR gene as a drug resistant gene. pKMA009-371/313-mCλ vector is such that the VL region of scFv371 or scFv313 and the mouse Cλ constant region are inserted downstream CAG promoter. pKMA010-371-mCg1 and pKMA009-371-mCλ vectors are as a whole referred to as chimeric 371 antibody expression vector. pKMA010-313-mCg1 and pKMA009-313-mCλ vectors are as a whole referred to as chimeric 313 antibody expression vector.

Using VH region or VL region of scFv371 and scFv313 as a template, mutation was introduced using site-directed mutagenesis to prepare VH region and VL region of 371M antibody and 313M antibody designed in Example 8. In the same manner as described above, expression vectors of these antibodies having mouse constant region (hereinafter referred to as "chimeric 371M antibody" and "chimeric 313M antibody") were constructed. pKMA010-371M/313M-mCg1 vector is such that the VH region of 371M or 313M and the mouse Cγ1 constant region are inserted downstream CAG promoter. pKMA009-371M/313M-mCλ vector is such that the VL region of 371M or 313M and the mouse Cλ constant region are inserted downstream CAG promoter. pKMA010-371M-mCg1 and pKMA009-371M-mCλ are as a whole referred to as chimeric 371M antibody expression vector. pKMA010-313M-mCg1 and pKMA009-313M-mCλ are as a whole referred to as chimeric 313M antibody expression vector.

Next, vectors expressing 371M antibody and 313M antibody having human constant region (hereinafter referred to as "human 371M antibody" and "human 313M antibody", respectively) were constructed as described below. Using as a template the chimeric 371M antibody expression vector and the chimeric 313M antibody expression vector constructed above, a region containing VH and VL of 371M and 313M in the combination as shown in the following table was amplified by PCR. Table 6 shows a combination of primers and SEQ ID NOs.

TABLE 6

| | VH | | VL | |
|---|---|---|---|---|
| | 5'- | 3'- | 5'- | 3'- |
| 371M | 371-VH-Fw SEQ ID NO: 19 | 371-VH-Rv SEQ ID NO: 20 | 371/313-VL-Fw SEQ ID NO: 21 | 371/313-VL-Rv SEQ ID NO: 22 |
| 313M | 313M-VH-Fw SEQ ID NO: 25 | 313-VH-Rv SEQ ID NO: 24 | 371/313-VL-Fw SEQ ID NO: 21 | 371/313-VL-Rv SEQ ID NO: 22 |

The amplified sequence of VH region was introduced into the vector pKMA010-hCg1 (previously treated with XhoI and BamHI) expressing human Cγ1 constant region and the amplified sequence of VL region was introduced into the vector pKMA009-hCL (previously treated with XhoI and BamHI) expressing human Cλ constant region, using In-fusion enzyme (Clontech). pKMA010-371/313-hCg1 vector is such that the H chain sequence of 371M or 313M antibody is inserted downstream CAG promoter and has DHFR gene as a drug resistant gene. pKMA009-371/313-hCL vector is such that the L chain sequence of 371M or 313M antibody is inserted downstream CAG promoter. pKMA010-371-hCg1 and pKMA009-371-hCL are as a whole referred to as human 371M antibody expression vector. pKMA010-313-hCg1 and pKMA009-313-hCL are as a whole referred to as human 313M antibody expression vector. Relationship between various vectors and the inserted sequences is shown in the following table.

TABLE 7

| Chimeric 371 antibody expression vector | pKMA010-371-mCg1 | 371 VH/mouse Cγ1 constant region |
|---|---|---|
| | pKMA009-371-mCλ | 371 VL/mouse Cλ constant region |
| Chimeric 313 antibody expression vector | pKMA010-313-mCg1 | 313 VH/mouse Cγ1 constant region |
| | pKMA009-313-mCλ | 313 VL/mouse Cλ constant region |
| Chimeric 371M antibody expression vector | pKMA010-371M-mCg1 | 371M VH/mouse Cγ1 constant region |
| | pKMA009-371M-mCλ | 371M VL/mouse Cλ constant region |
| Chimeric 313M antibody expression vector | pKMA010-313M-mCg1 | 313M VH/mouse Cγ1 constant region |
| | pKMA009-313M-mCλ | 313M VL/mouse Cλ constant region |
| Human 371M antibody expression vector | pKMA010-371M-hCg1 | 371M VH/human Cγ1 constant region |
| | pKMA009-371M-hCL | 371M VL/human Cλ constant region |
| Human 313M antibody expression vector | pKMA010-313M-hCg1 | 313M VH/human Cγ1 constant region |
| | pKMA009-313M-hCL | 313M VL/human Cλ constant region |

Freestyle293F cells (Invitrogen) were transfected with vectors expressing H chain and L chain of chimeric 371, 313, 371M and 313M antibodies and human 371M and 313M antibodies using Neofection (ASTEC Co., Ltd.) and were subject to shaking culture at 37° C. under environmental conditions of 8% $CO_2$ at 125 rpm for expression of various antibodies. On the fifth day of culture, the culture supernatant was collected and purified by chromatography using HiTrap rProteinA FF (GE Healthcare). The elution fraction containing each antibody was dialyzed against PBS (SIGMA) to provide the purified form of chimeric 371 antibody, chimeric 313 antibody, chimeric 371M antibody, chimeric 313M antibody, human 371M antibody and human 313M antibody, respectively.

EXAMPLE 10

Epitope Analysis of 371M Antibody

For more fully analyzing the epitope of 371M antibody, the reactivity analysis of 371M antibody was performed using the TTR alanine-substitution variant constructed in Example 3. *E. coli* strain M15 was transfected with the TTR variant expression vector constructed in Example 3 and cultured in 20 mL of LB/Ampicillin (50 μg/mL)/Kanamycin (25 μg/mL) at 37° C. At the point of O.D.600 nm=0.5, IPTG was added at a final concentration of 1 mM and the culture was continued overnight. The culture was centrifuged and the precipitate fraction was solubilized with Bugbuster (Merck). The solubilized cell suspension was electrophoresed on 8-16% SDS-PAGE gel and transferred to Immobilon-P (Millipore) from the gel. The transferred membrane was added with 2% Skimmilk-PBST and shaken at room temperature for 1 hour for blocking the membrane. Chimeric 371M antibody was diluted with 2% Skimmilk-PBST at a concentration of 1 μg/mL and the membrane was added with 10 mL of the diluent and shaken at room temperature for 1 hour. The membrane was washed with PBST, added with a detection antibody HRP-labelled anti-mouse IgG(H+L) (AMERICAN QUALEX INTERNATIONAL), which was previously diluted 5000-folds with 2% Skimmilk-PBST, and was shaken at room temperature for 1 hour. After washing with PBST, color development was conducted with Ez West Blue (ATTO).

Figure 2:
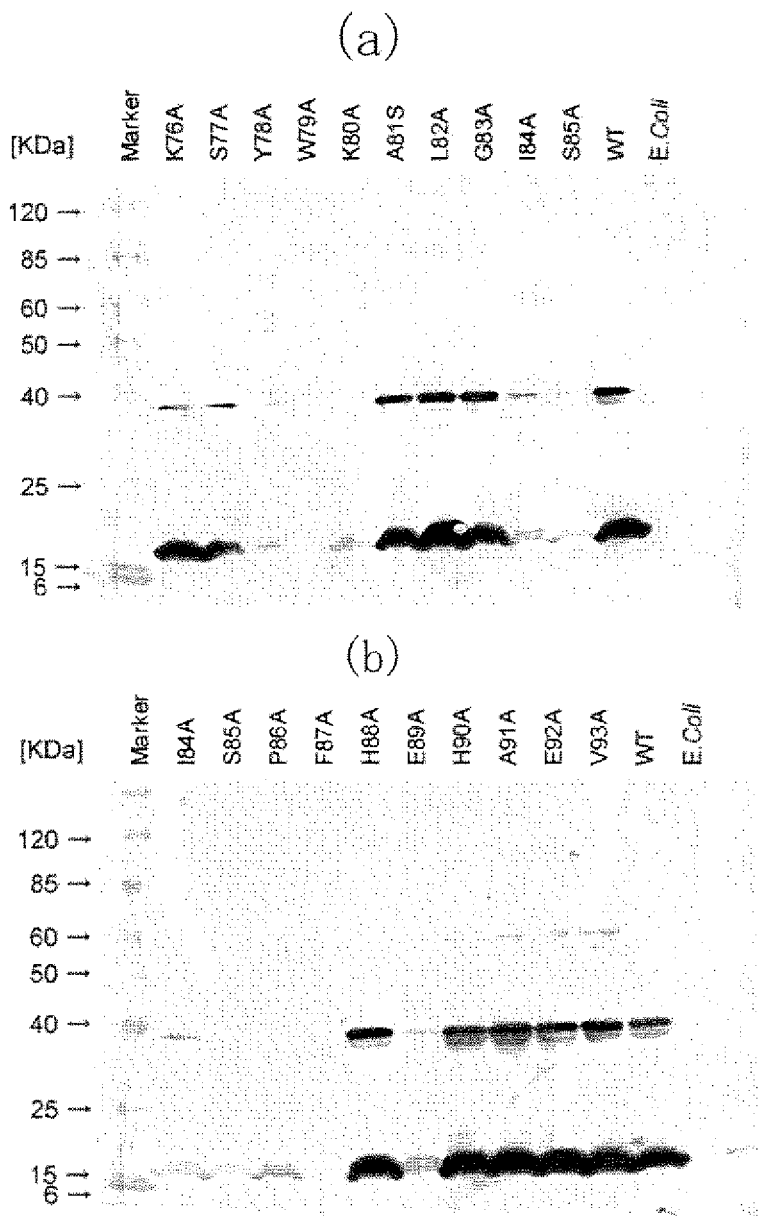
FIG. 2 shows the results of epitope analysis for (a) positions 76-85 of TTR; and (b) positions 84-93 of TTR, respectively.

As a result, as shown in FIG. 2, it was found that 371M antibody had an epitope at positions 78-89 of human TTR.

EXAMPLE 11

Reaction Specificity Analysis of 371M Antibody and 313M Antibody

For analyzing the reactivity of 371M antibody and 313M antibody to TTR tetramer, reaction specificity analysis was performed using surface plasmon resonance. Using Biacore2000 (GE Healthcare), around each 1,000 RU of WT TTR tetramer, V30M TTR tetramer and V30M TTR fibril (prepared in Examples 4 and 6; recombinant) was immobilized on Sensorchip CM5 (GE Healthcare). Immobilization of the ligand was performed with 10 mM acetate buffer (pH 6.0). Polyclonal Rabbit Anti-Human Prealbumin (Dako), chimeric 371M antibody, chimeric 313M antibody and negative control antibody, which were diluted with HBS-EP Buffer at 10 μg/mL, were migrated at 20 μL/min for 2 minutes. After migration, dissociation was carried out for 60 minutes and regeneration was performed with 10 mM Gly-NaOH (pH 9.0) for 30 seconds.

Figure 3:
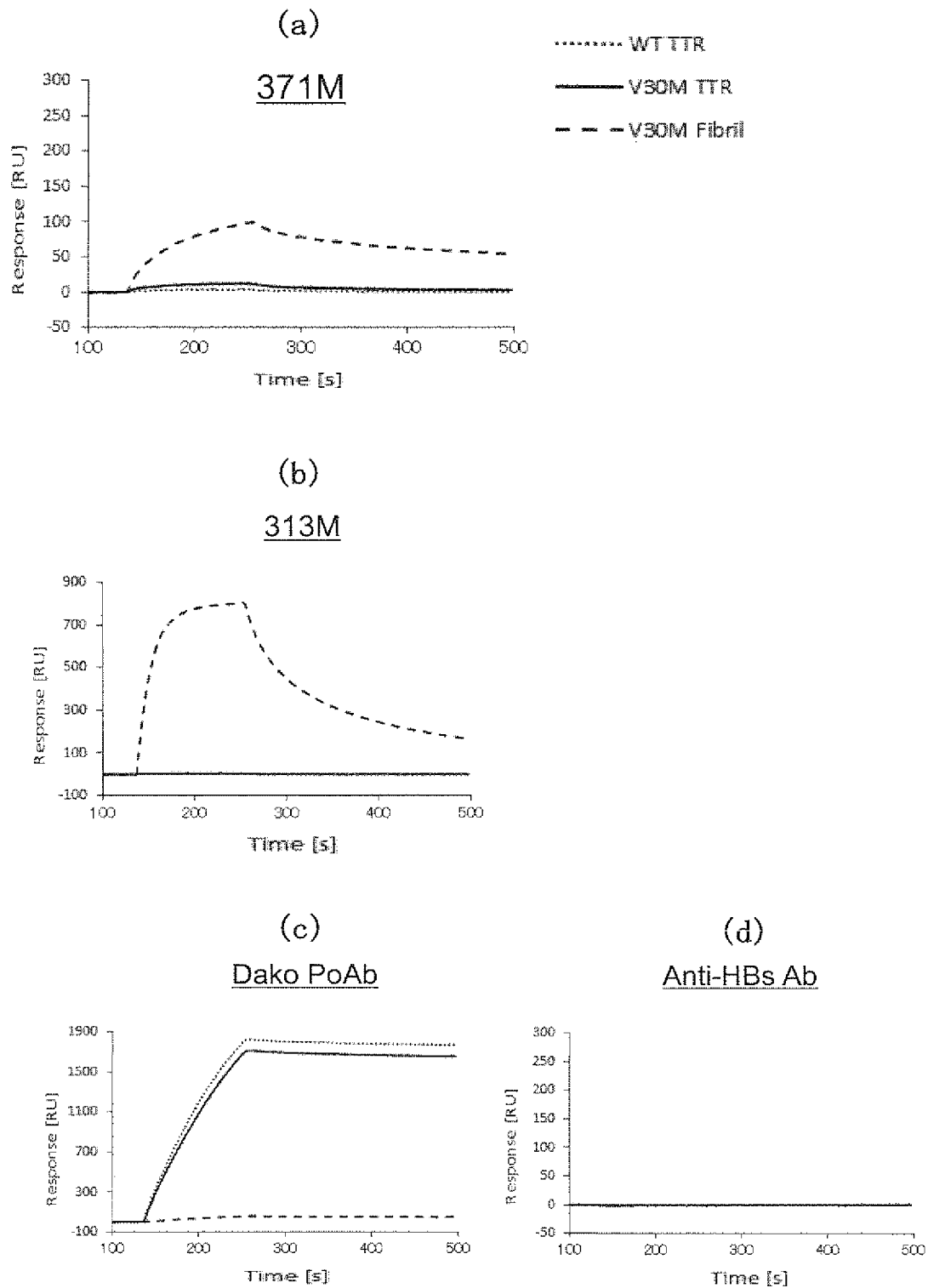
FIG. 3 shows the results of reaction specificity analysis using surface plasmon resonance for (a) 371M antibody, (b) 313M antibody, (c) polyclonal antibody manufactured by Dako, and (d) negative control antibody, respectively.

As a result, as shown in FIG. 3, it was revealed that 371M antibody and 313M antibody did not react with WT TTR and V30M tetrameric TTRs but specifically recognized V30M fibril ((a) and (b)). Polyclonal antibody manufactured by Dako strongly reacted with WT TTR and V30M TTR and weakly reacted with V30M TTR fibril (c). Negative control antibody reacted with none of the TTRs (d).

EXAMPLE 12

Reactivity Analysis of 371 Antibody and 313 Antibody to Patient Sera

Analysis was conducted to investigate whether 371 antibody and 313 antibody show the reactivity to sera from FAP patients. It is a preferable property for an antibody for FAP therapy that the administered antibody does not recognize human TTR in patient sera. Sera from healthy adults and sera from FAP patients having V30M TTR variant at 2 µg/mL and fibril of wild-type TTR from sera treated with an acid as in Example 6 and TTR amyloid extracted from the spleen of FAP patients at about 4 µg/mL were added to Maxisorp plate (Nunc) at 100 µL/well for immobilization of the antigens. Each 300 µL/well of 1% BSA-PBS was added to the immobilized plate and incubated at room temperature for 1 hour for blocking the plate. Chimeric 371 antibody and chimeric 313 antibody were serially diluted with 1% BSA-PBS and each 100 µL of the diluent was added to each well of the plate and incubated at 37° C. After 1 hour, the well was washed with PBST and each 100 µL of the detection antibody anti-mouse IgG(H+L)/HRP (Zymed) was added to each well of the plate and incubated at 37° C. After 1 hour, the well was washed with PBST and each 100 µL of TMB (SIGMA) was added to each well of the plate for development. After 30 minutes, the reaction was quenched with 1N sulfuric acid and color development value (O.D. 450 nm) was measured with a microplate reader (Molecular Devices).

Figure 4:
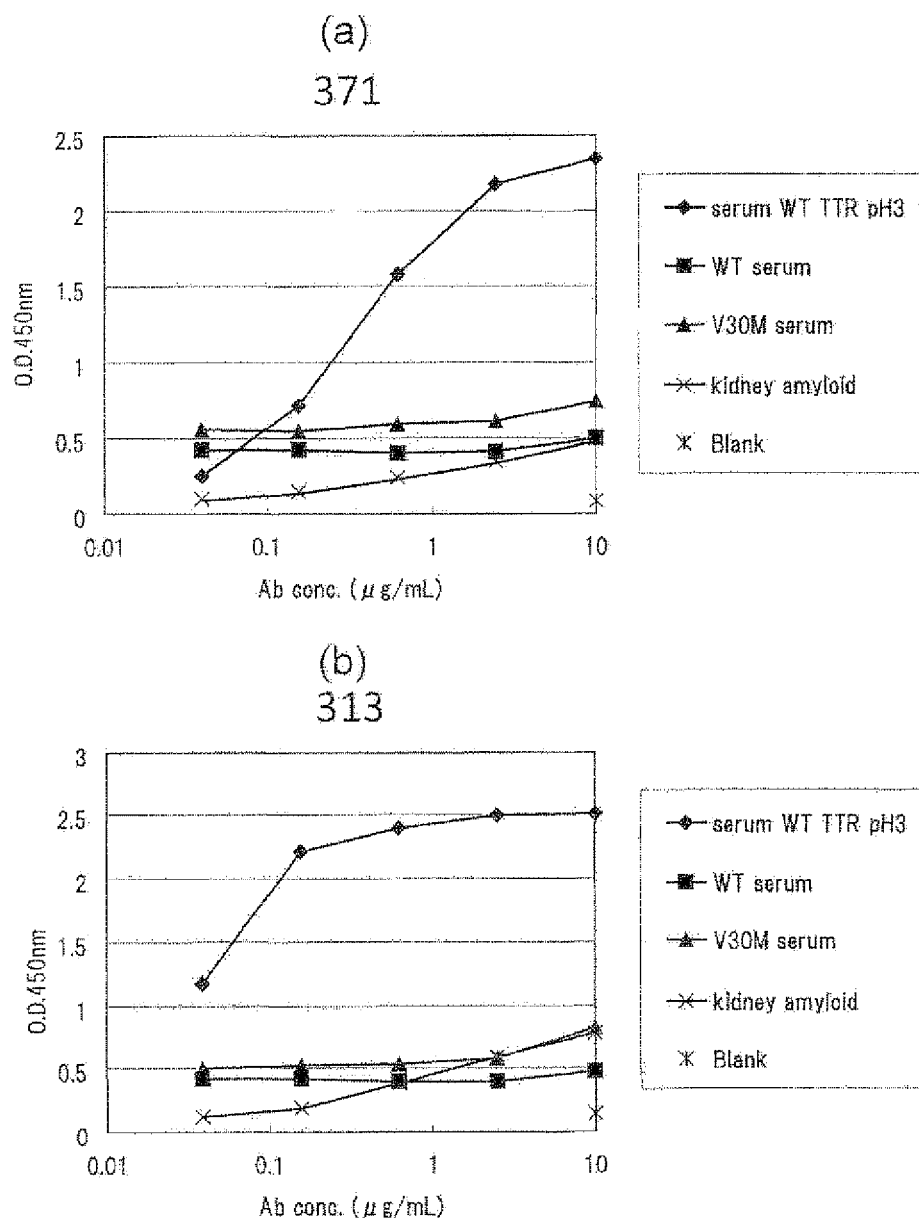
FIG. 4 shows the results of reactivity analysis to patient sera for (a) 371 antibody, and (b) 313 antibody, respectively.

As a result, as shown in FIG. 4, 371 antibody (a) and 313 antibody (b) clearly showed the reactivity to TTR amyloid from FAP patients and to amyloid formed by acid treatment of wild-type TTR from sera in a concentration-dependent manner but not to sera from healthy adults and from FAP patients.

EXAMPLE 13

Reactivity Analysis of 371M Antibody and 313M Antibody to Patient Tissues

The heart was removed from FAP patients having V30M TTR and formalin fixed. The fixed heart tissue was embedded in paraffin block to prepare tissue section. After the tissue section was sliced to a thickness of 4 µm and attached to an object glass, deparaffinization treatment was conducted. After washing with PBS, the tissue section was infiltrated to 0.1% periodic acid dihydrate for 10 minutes and further washed with PBS. The tissue section was immersed in Rabbit serum (Dako) diluted 50-folds with 0.5% BSA-PBS for 1 hour for blocking. After washing with PBS, the tissue section was immersed in chimeric 371 antibody/chimeric 313 antibody/chimeric 371M antibody/chimeric 313M antibody/negative control antibody as a primary antibody, which were diluted with 0.5% BSA-PBS to 10 µg/mL, at 4° C. overnight. The tissue section was then immersed in HRP-labelled Rabbit anti-mouse IgG (Dako) as a secondary antibody, which was diluted 100-folds with 0.5% BSA-PBS, at room temperature for 1 hour. After washing with PBS, development with DAB was conducted. Hematoxylin staining was also done. For positive control, the same procedures were performed using Polyclonal Rabbit Anti-Human Prealbumin (Dako) as a primary antibody and HRP-labelled Goat anti-Rabbit IgG (Dako) as a secondary antibody. Besides, taking into consideration the possibility that TTR is denatured by formalin fixation to thereby alter its steric structure, frozen tissue section of the heart of FAP patients having V30M TTR was also subject to immunostaining in like manner. Furthermore, for confirming the presence of amyloid fibril, Congo red staining was also conducted. Congo red is known to attach to amyloid fibril to thereby cause short-wavelength shift.

Figure 5:
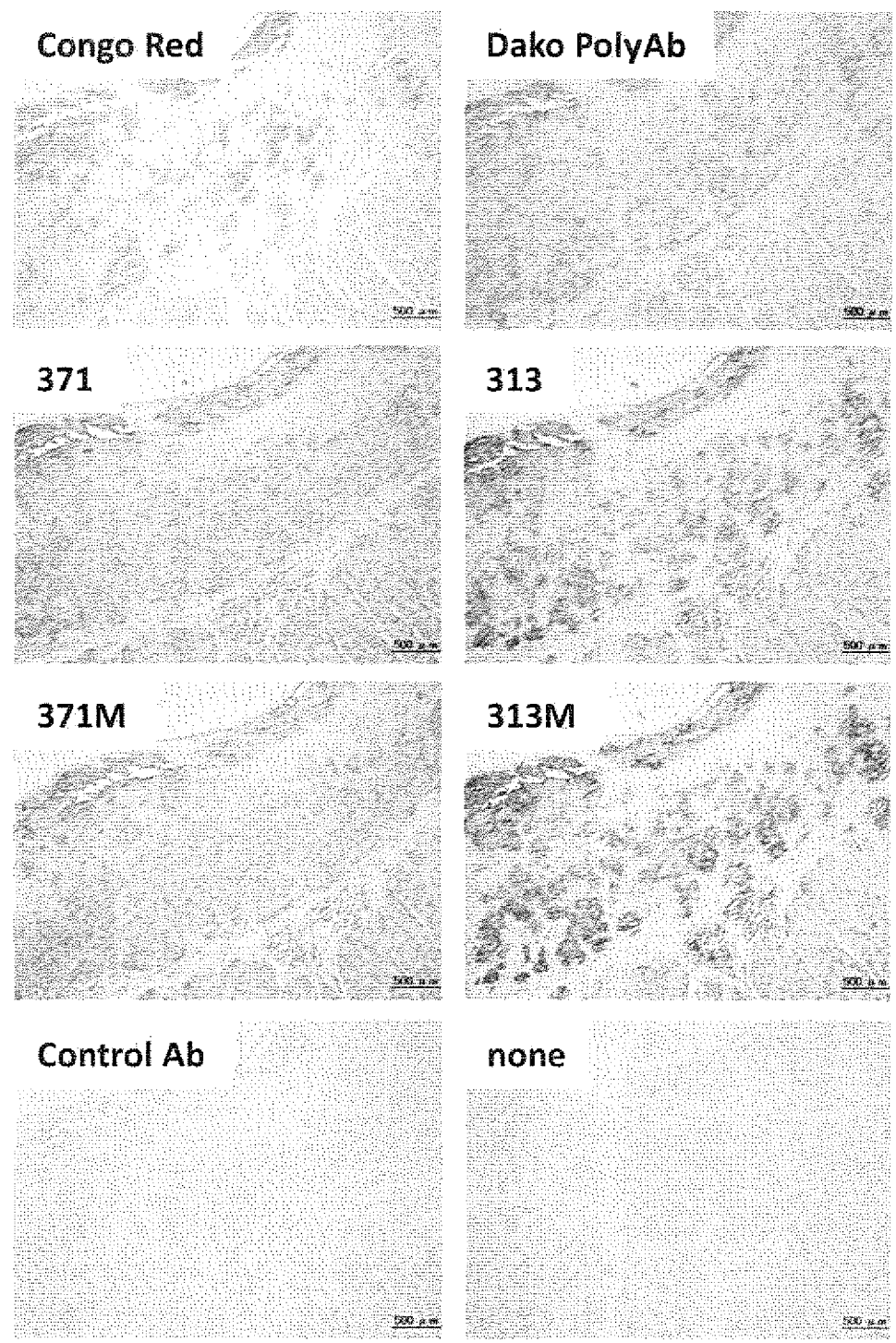
FIG. 5(a) shows the results of reactivity analysis to patient tissue (paraffin section).
FIG. 5(b) shows the results of reactivity analysis to patient tissue (frozen section).
Figure 5:
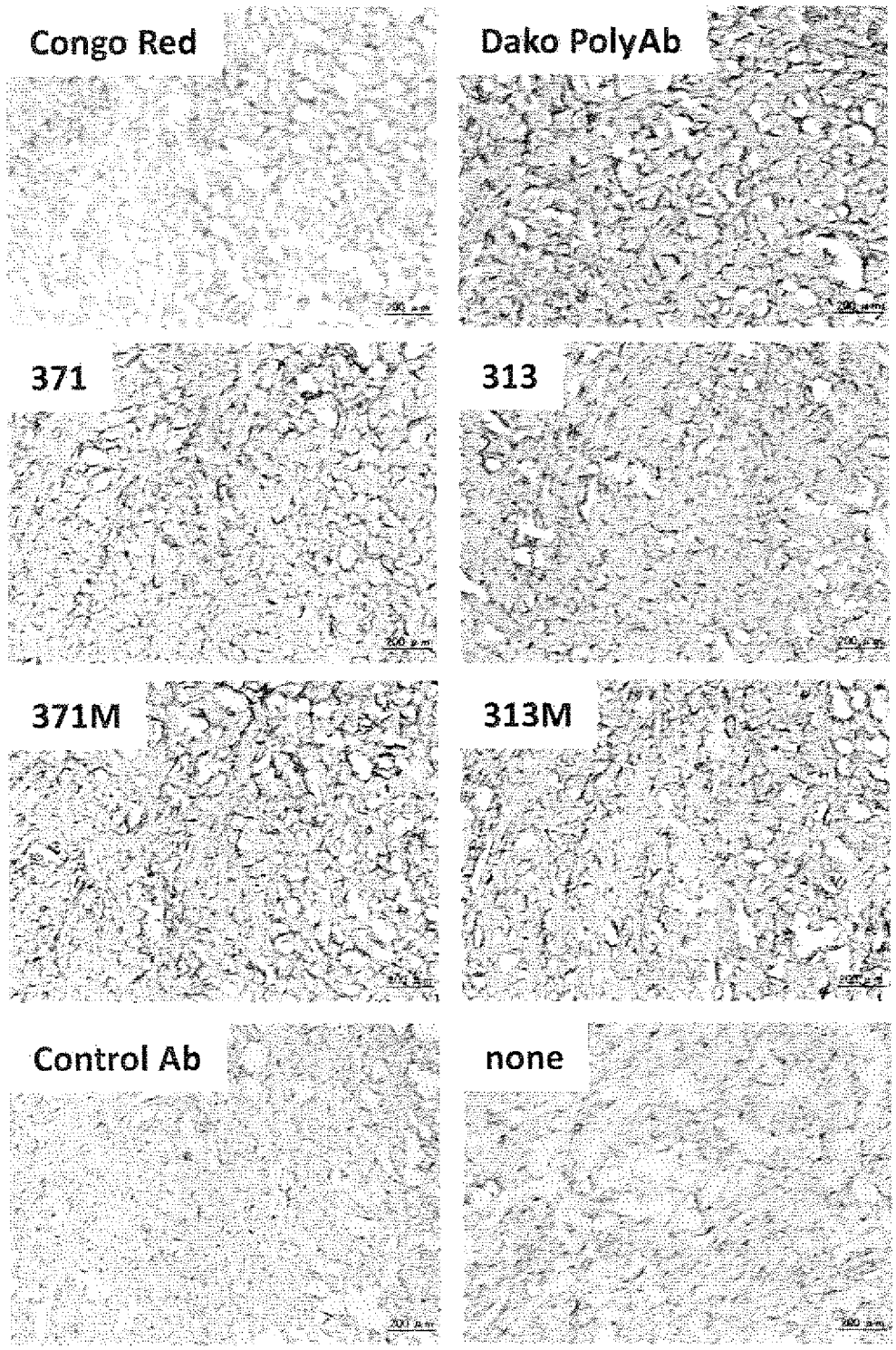

As a result, as shown in FIG. 5, it was confirmed that 371 antibody/313 antibody/371M antibody/313M antibody specifically recognized TTR deposited in the heart from FAP patients in both the paraffin section (FIG. 5a) and the frozen section (FIG. 5b).

EXAMPLE 14

Reactivity Analysis of 371M Antibody and 313M Antibody to TTR Fibril

Each 1.5 µg of seven kinds of the TTR fibrils prepared in Example 6 and the purified wild-type TTR was electrophoresed on 8-16% SDS-PAGE gel and transferred to Immobilon-P (Millipore) from the gel. The transferred membrane was added with 2% Skimmilk-PBST and shaken at room temperature for 1 hour for blocking the membrane. Chimeric 371M antibody or chimeric 313M antibody was diluted with 2% Skimmilk-PBST at a concentration of 1 µg/mL and the membrane was added with 10 mL of the diluent and shaken at room temperature for 1 hour. The membrane was washed with PBST, added with a detection antibody anti-mouse IgG(H+L), which was previously diluted 5000-folds with 2% Skimmilk-PBST, and was shaken at room temperature for 1 hour. After washing with PBST, color development was conducted with Ez West Blue (ATTO).

Figure 6:
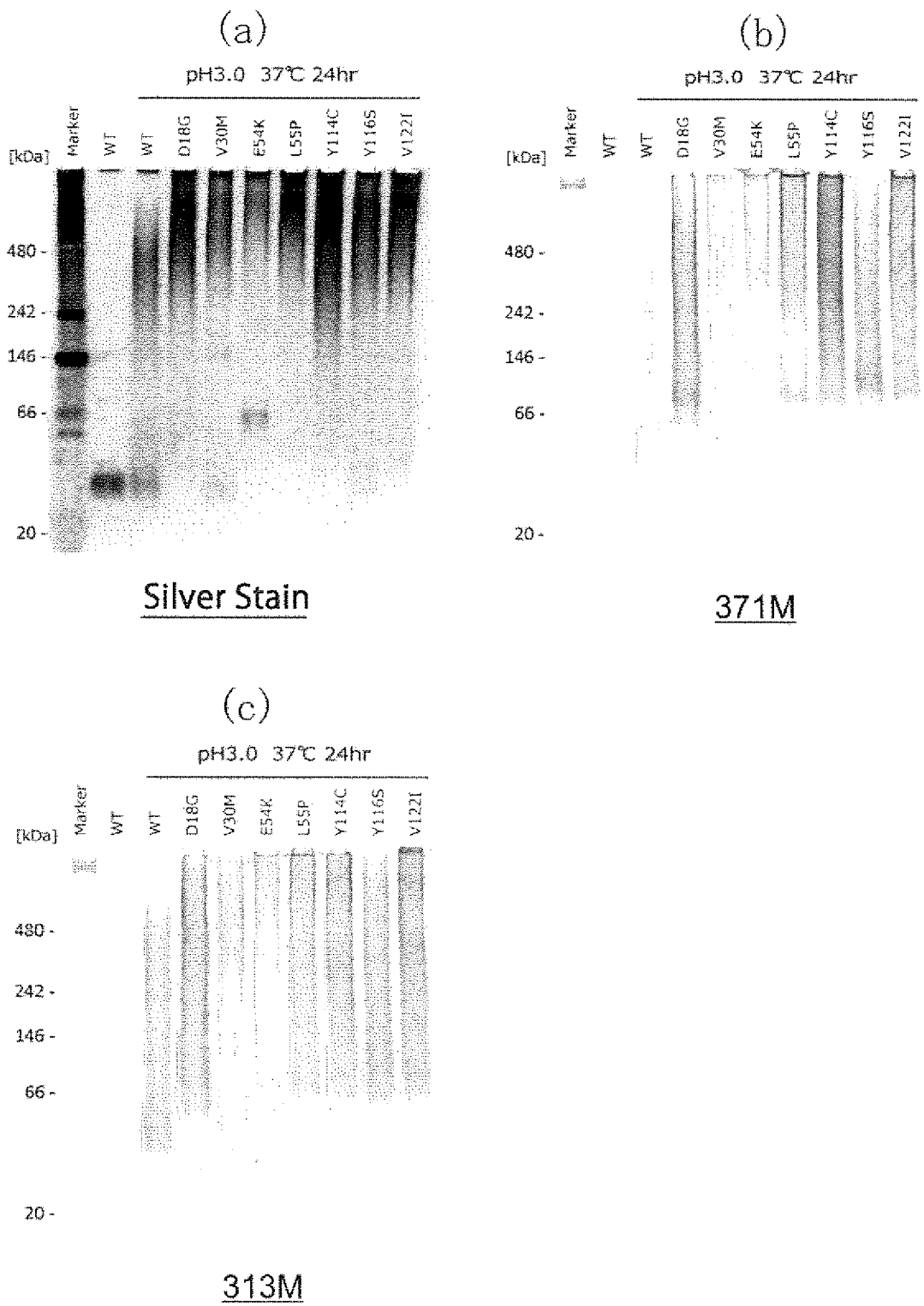
FIG. 6 shows the results of reactivity analysis to TTR fibril for (a) silver stain, (b) Western blotting with 371M antibody, and (c) Western blotting with 313M antibody, respectively.

As a result, as shown in FIG. 6, it was found that 371M antibody and 313M antibody recognized various TTR fibrils but on the other hand did not recognize purified wild-type TTR.

EXAMPLE 15

Construction of Measurement System for Inhibitory Activity to V30M TTR-fibrillization Recombinant V30M TTR was diluted with PBS(−) to 375 µg/mL and mixed with four kinds of surfactants at a final concentration of 0.1%, 0.01% and 0.001%. The surfactants used were (1) benzalkonium chloride (Yamazen Corporation), (2) sodium deoxycholate (Nacalai Tesque), (3) Zwittergent3-16 (Carbiochem), and (4) NP-40 (Wako). The mixtures were left to stand at 37° C. for 4 days and fluorescence intensity was measured by ThioflavinT assay (excitation wavelength 440 nm, fluorescent wavelength 480 nm) to evaluate a degree of TTR-fibrillization.

Figure 7:
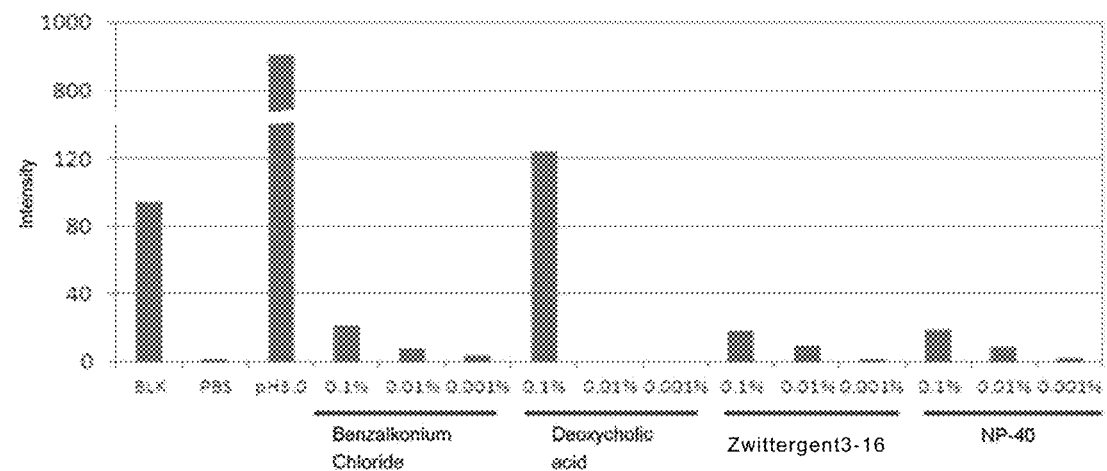
FIG. 7 shows the results of preliminary examination of TTR-fibrillization inhibition test.

The results of ThioflavinT assay are shown in FIG. 7. For any of the surfactants, TTR-fibrillization progressed when used at a concentration of 0.1%. Among others, it was found that TTR-fibrillization progressed most rapidly when sodium deoxycholate was used. Next, an optimum concentration of sodium deoxycholate was investigated. Recombinant V30M TTR was diluted with PBS(−) to 375 µg/mL and mixed with sodium deoxycholate at a concentration of 1%, 0.5%, 0.2%, 0.1% and 0.01%. The mixtures were left to stand at 37° C. and, after 4 days and 7 days, ThioflavinT assay was conducted to evaluate a degree of TTR-fibrillization.

Figure 8:
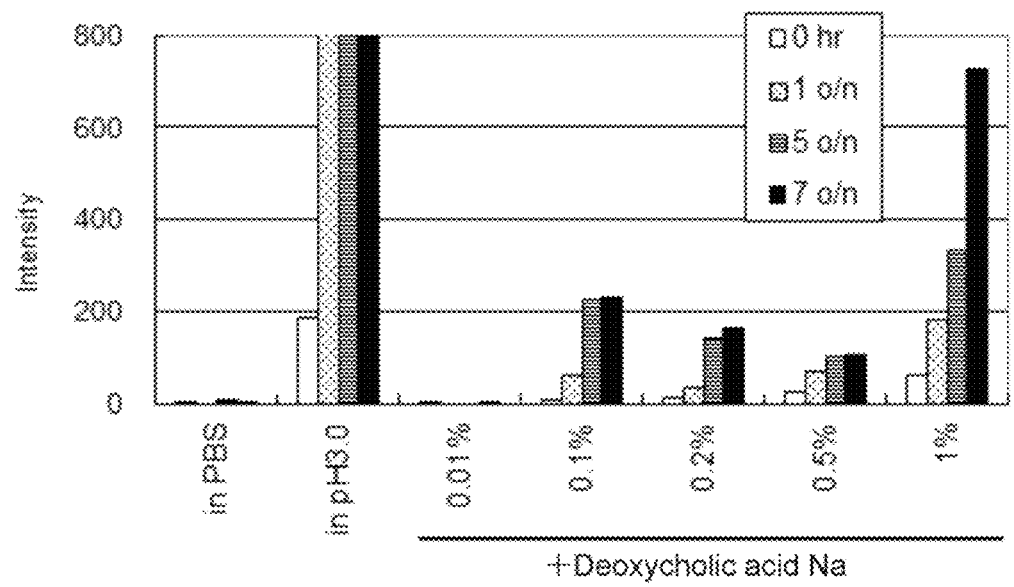
FIG. 8 shows the results of preliminary examination of TTR-fibrillization inhibition test.

The results are shown in FIG. 8. The most remarkable fibrillization was observed under the conditions of 1% of a concentration of sodium deoxycholate. However, since fibrillization was observed even at 0 hour (immediately after addition), it was thought that progress of fibrillization was too rapid. To the contrary, under the conditions of 0.1%, fibrillization was observed after the mixtures were left to stand overnight or for a longer period of time and remarkable progress of fibrillization most depending on treatment time was observed as compared to the conditions of 0.5%, 0.2% and 0.01%. From these, it was found that the optimum concentration of sodium deoxycholate was 0.1%. Up till the present, the conditions under which fibrillization of V30M TTR progresses under the circumstance of neutral pH have not yet been reported and thus fibrillization of TTR was made to progress by placing TTR under acidic pH circumstances such as pH 3.0. On the other hand, since an antibody is denatured and loses its activity when it is exposed to acidic circumstances, it has been difficult to evaluate the inhibitory ability of anti-TTR antibody to TTR-fibrillization. In accordance with the present invention, it has newly been found that fibrillization of V30M TTR progresses even under neutral circumstances by introducing sodium deoxycholate into the system to thereby succeed in constructing the system which allows for evaluation of the inhibitory ability of anti-TTR antibody to fibrillization.

EXAMPLE 16

V30M TTR-fibrillization Inhibition Test of 371M Antibody and 313M Antibody

Purified V30M TTR, and 371 antibody, 313 antibody, 371M antibody, 313M antibody or negative control antibody were mixed together at a molar ratio of 10 µM:0.01 to 2 µM (TTR: 550 µg/mL, antibodies: 1.5 to 300 µg/mL) and the mixture was left to stand under PBS+0.1% sodium deoxycholate at 37° C. for 3 days. Using the samples after being left to stand, ThioflavinT assay (excitation wavelength 440 nm, fluorescent wavelength 480 nm) was performed to measure fluorescence intensity.

Figure 9:
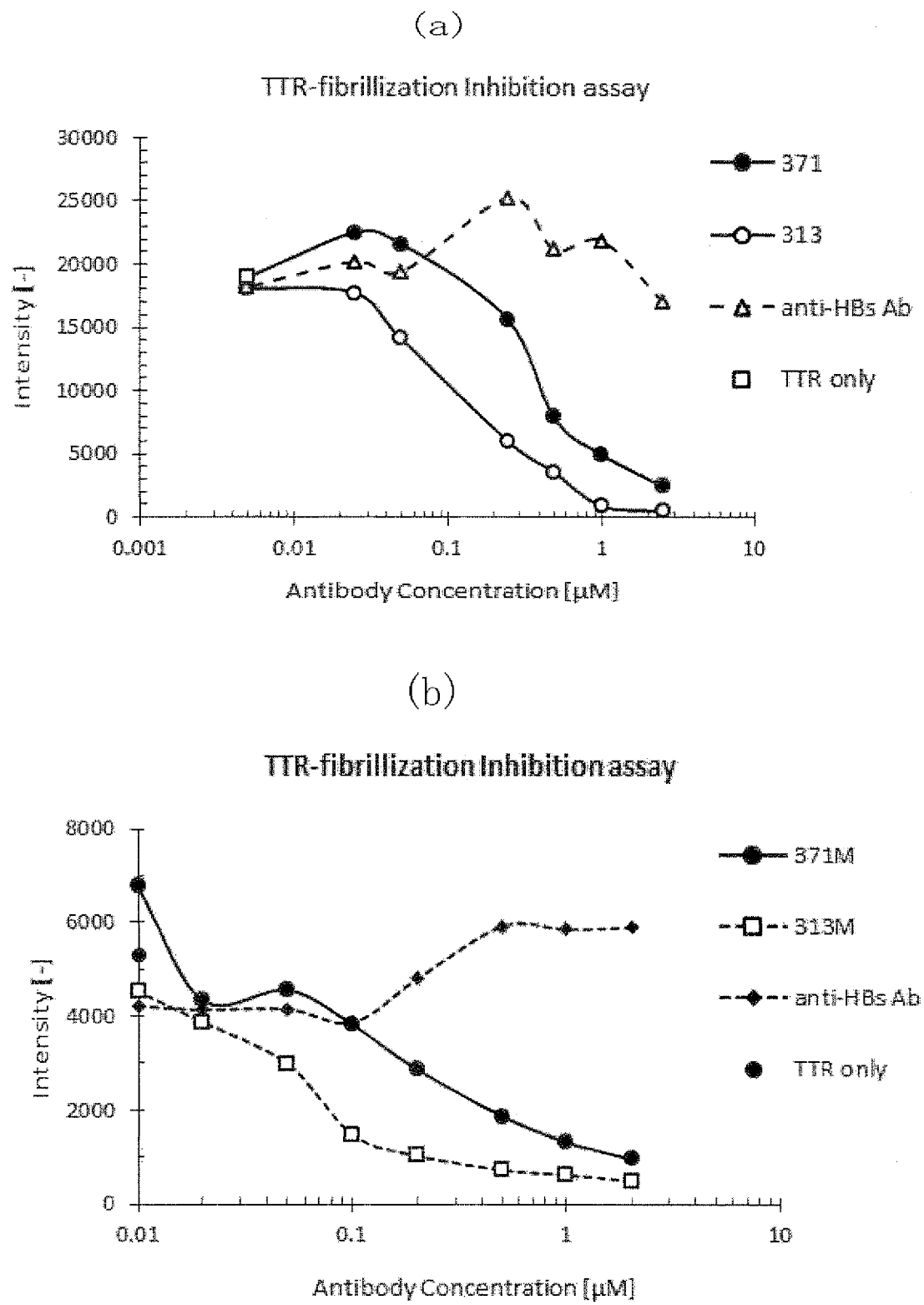
FIG. 9 shows the results of TTR-fibrillization inhibition test for (a) 371 antibody and 313 antibody, and (b) 371M antibody and 313M antibody, respectively.

As a result, as shown in FIG. 9, it was found that 371, 313, 371M and 313M antibodies had the activity to inhibit fibrillization of V30M TTR in an antibody concentration-dependent manner.

EXAMPLE 17

Macrophage Phagocytic Ability Test

To investigate whether 371M antibody and 313M antibody promote the ability of macrophage to phagocytose TTR fibril, macrophage phagocytic ability test was performed. This test mimics the process where macrophage removes TTRs deposited in the tissues of TTR patients. If the phagocytic ability of macrophage is promoted by the addition of these antibodies, it is expected that these antibodies have the activity to promote removal of TTR deposition in human tissues.

Human iPS cells were prepared from the skin tissue from healthy adults in accordance with the method described in Non-patent reference 16 and further differentiated into macrophages (iPS-MP). iPS-MPs (1 to 2×10$^6$ cells) were cultured in the presence of 50 ng/mL hGM-SCF and 25 µg/mL M-CSF in 10 cm dish for 24 hours. iPS-MPs were washed with PBS, then incubated in a medium containing 20 µg/mL of mitomycin C at 37° C. for 10 minutes to suspend the cell proliferative ability and added to 96-well plate at 5×10$^4$ cells/100 µL/well. V30M TTRs, untreated or acid treated for 24 hours, were diluted with the culture medium to 3.2 µg/mL and each 50 µL of the dilution was added. In addition, PBS/human 371M antibody/human 313M antibody/negative control antibody were diluted to 40 g/mL and each 50 µL was added. Culture was continued at 37° C. under 5% $CO_2$ for 2 days and thereafter culture supernatant was collected.

A residual quantity of TTR after culture was quantified by ELISA as described below to evaluate the phagocytic ability of macrophage. A 96-well plate was added with each 5 µL of the culture supernatant and with 100 µL of a coating solution (25 mM sodium carbonate buffer) and thereafter was left to stand at 4° C. overnight. After washing with PBST, 250 µL of a blocking solution (a solution of 0.5% gelatin dissolved in the coating solution) was added and the plate was incubated at room temperature for 1 hour. After washing with PBST, Polyclonal Rabbit Anti-Human Prealbumin (Dako) was diluted 1,000-folds with 0.05% gelatin-PBST, each 100 µL of the dilution was added and the plate was incubated at room temperature for 1 hour. After washing with PBST, HRP-labelled Goat anti-Rabbit IgG (Dako) was diluted 5,000-folds with 0.05% gelatin-PBST, each 100 µL of the dilution was added and the plate was incubated at room temperature for 1 hour. After washing with PBST, development was performed with 100 µL of SureBlue (KPL) for 5 minutes and stopped with 100 µL of 1 M hydrochloric acid. A wavelength at 450 nm was measured with xMARK microplate reader (Bio-Rad Laboratories).

Figure 10:
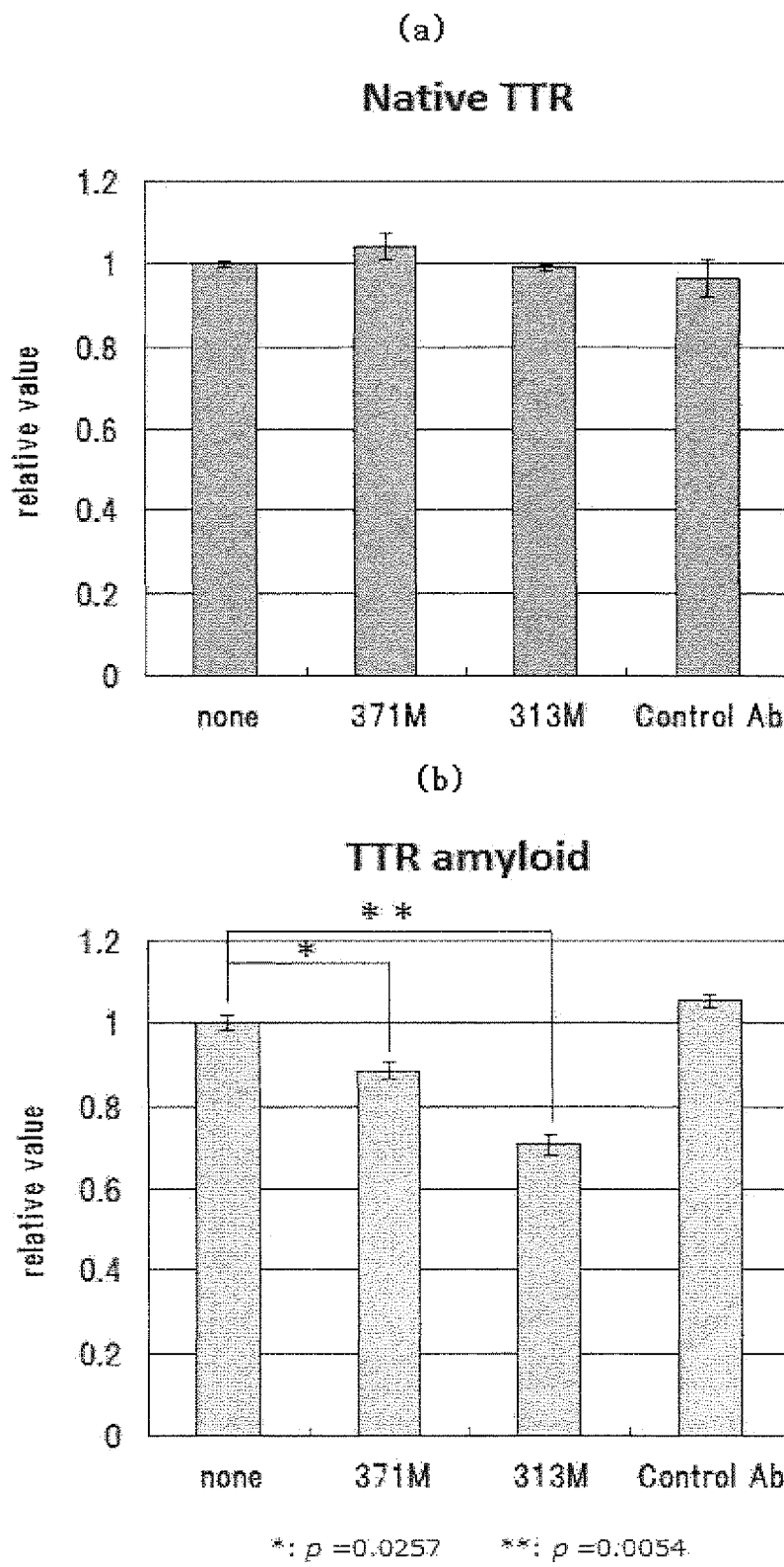
FIG. 10 shows the results of macrophage phagocytic ability test for (a) untreated purified V30M, and (b) TTR fibril, respectively.

The results are shown in FIG. 10. For untreated purified V30M, no statically significant difference in a residual quantity of TTR could be seen between the samples (a). To the contrary, it was found that, for TTR fibril, statistically significant reduction in a residual quantity of TTR was observed for 371M antibody and 313M antibody as compared to PBS (none)(b), demonstrating that 371M antibody and 313M antibody had the activity to promote the phagocytic activity of iPS cell-differentiated macrophages to TTR fibril.

EXAMPLE 18

Drug Efficacy Evaluation Test Using V30M Tg Rat

Using V30M Tg rat (Non-patent reference 14; transgenic rat where a gene of human TTR with mutation of valine at position 30 to methionine in the amino acid sequence of TTR is introduced), each 10 mg/kg of chimeric 371 antibody and chimeric 313 antibody or PBS was administered for 6 months, from 3-month old to 9-month old, each group consisting of 7 or 8 rats, once per week 26 times in total. After administration, the large intestine was taken out by autopsy and formalin fixed. The fixed tissue of the large intestine was embedded in a paraffin block to prepare tissue section. The tissue section was subject to immunostaining using Polyclonal Rabbit Anti-Human Prealbumin (Dako) as a primary antibody and HRP-labelled Goat anti-Rabbit IgG (Dako) as a secondary antibody and a degree of TTR deposition in the muscular layer of the large intestine was digitized and compared between the groups.

Figure 11:
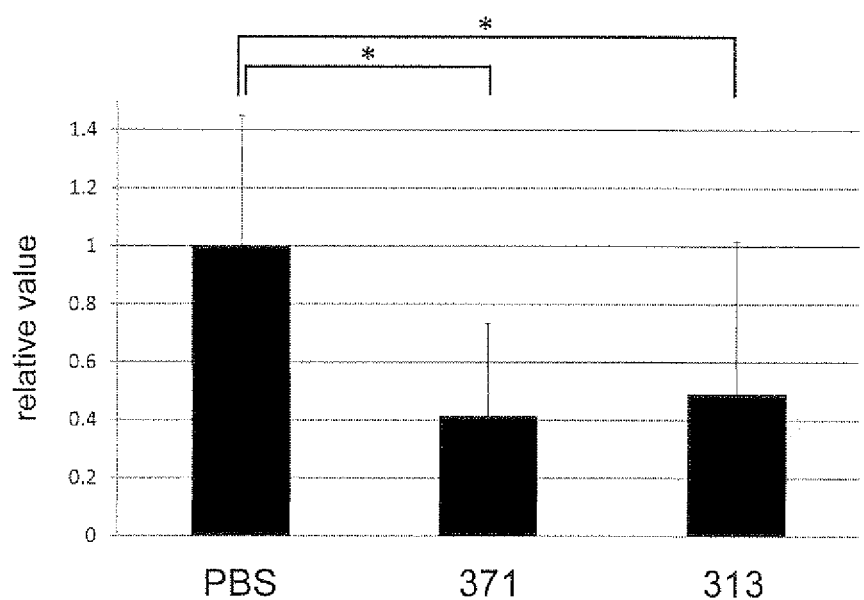
FIG. 11 shows the results of drug efficacy evaluation test using V30M Tg rat.

As a result, as shown in FIG. 11, TTR deposition was significantly suppressed in the group of 371 antibody administration and the group of 313 antibody administration as compared to the group of PBS administration.

INDUSTRIAL APPLICABILITY

The recombinant human anti-transthyretin antibody of the present invention, as being excellent in its activity (the inhibitory activity to TTR fibrillization, the activity to promote the phagocytic ability of macrophage, etc.) and/or specificity (specifically recognizes TTRs with structural change and TTR fibril), is useful as an effective medicament to various diseases associated with structural change or fibrillization of TTR.

The invention claimed is:

1. A human antibody having the activity to inhibit fibrillization of transthyretin (TTR), wherein the antibody binds to a TTR amyloid derived from two or more kinds of variant TTRs, and wherein the variant TTR is TTR having a mutation selected from the group consisting of D18G, V30M, E54K, L55P, Y114C, Y116S and V122I, the antibody comprising the heavy chain complementarity determining regions (CDRs) of (a) or the sequence of (b) below and the light chain CDRs of (c) or the sequence of (d) below:
   (a) SEQ ID NOs: 1 to 3;
   (b) SEQ ID NO: 13;
   (c) SEQ ID NOs: 4 to 6; and
   (d) SEQ ID NO: 14.

2. The human antibody of claim 1 which specifically recognizes TTRs with structural change.

3. The human antibody of claim 1 which specifically binds to TTR amyloid.

4. The human antibody of claim 1 which promotes removal of TTR amyloid.

5. The human antibody of claim 1 which promotes the phagocytic ability of macrophages to TTR amyloid.

6. The human antibody of claim 1 wherein an epitope is a sequence comprising position 79 to position 89 of TTR.

7. The human antibody of claim 6 wherein an epitope is position 79 to position 89 of TTR.

8. The human antibody of claim 1 which inhibits TTR amyloidosis.

9. The human antibody of claim 8 wherein the TTR amyloidosis is in subjects with Familial Amyloidotic Polyneuropathy (FAP).

10. The human antibody of claim 8 wherein the TTR amyloidosis is in subjects with Senile Systemic Amyloidosis (SSA).

11. The human antibody of claim 1 which is an antibody obtained by phage display.

12. The human antibody of claim 1 comprising:
   (a) a heavy chain variable region fragment comprising the complementarity determining regions (CDRs) of SEQ ID NOs: 1, 2 and 3; or
   (b) a heavy chain variable region fragment comprising SEQ ID NO: 13; and
   (c) a light chain variable region fragment comprising a complementarity determining region of a light chain comprising CDRs SEQ ID NOs: 4, 5, and 6; or
   (d) a light chain variable region comprising SEQ ID NO: 14.

13. A TTR-fibrillization inhibitor comprising the antibody of claim 1.

14. A pharmaceutical composition for inhibiting TTR amyloidosis comprising the antibody of claim 1.

15. The pharmaceutical composition of claim 14 wherein the TTR amyloidosis is in subjects with FAP.

16. The pharmaceutical composition of claim 14 wherein the TTR amyloidosis is in subjects with SSA.

17. An H chain variable region fragment consisting of the polypeptide consisting of the amino acid sequence as shown in SEQ ID NO: 13.

18. An L chain variable region fragment consisting of the polypeptide consisting of the amino acid sequence as shown in SEQ ID NO: 14.

19. A single-chain variable region fragment of an antibody to TTR, which is formed by linking:
   (1) an H chain variable region fragment comprising a complementarity determining region of an H chain consisting of the polypeptide consisting of the amino acid sequence as shown in SEQ ID NOs: 1 to 3; or
   (2) an H chain variable region fragment consisting of the polypeptide consisting of the amino acid sequence as shown in SEQ ID NO: 13; and
   (3) an L chain variable region fragment comprising a complementarity determining region of an L chain consisting of the polypeptide consisting of the amino acid sequence as shown in SEQ ID NOs: 4 to 6; or
   (4) an L chain variable region fragment consisting of the polypeptide consisting of the amino acid sequence as shown in SEQ ID NO: 14.

* * * * *